US009725684B2

(12) United States Patent
Fernandes et al.

(10) Patent No.: US 9,725,684 B2
(45) Date of Patent: Aug. 8, 2017

(54) CAPSULES AND COMPOSITIONS COMPRISING THE SAME

(75) Inventors: Gregory E. Fernandes, Greenville, SC (US); Robert M. MacMeccan, Greer, SC (US)

(73) Assignee: Milliken & Company, Spartanburg, SC (US)

( * ) Notice: Subject to any disclaimer, the term of this patent is extended or adjusted under 35 U.S.C. 154(b) by 305 days.

(21) Appl. No.: 13/035,445

(22) Filed: Feb. 25, 2011

(65) Prior Publication Data

US 2012/0220515 A1 Aug. 30, 2012

(51) Int. Cl.

| | |
|---|---|
| ***A61K 9/48*** | (2006.01) |
| ***A61J 3/07*** | (2006.01) |
| ***C11D 7/60*** | (2006.01) |
| ***C11D 17/00*** | (2006.01) |

(52) U.S. Cl.
CPC ................................ *C11D 17/0039* (2013.01)

(58) Field of Classification Search
CPC ................. C11D 7/60; A61J 3/07; A61K 9/48
USPC ............................................... 8/137; 510/267
See application file for complete search history.

(56) References Cited

U.S. PATENT DOCUMENTS

| | | | |
|---|---|---|---|
| 3,301,439 A | | 1/1967 | Kosar et al. |
| 4,244,836 A | | 1/1981 | Frensch et al. |
| 4,898,781 A | | 2/1990 | Onouchi et al. |
| 5,225,117 A | | 7/1993 | Matsushita |
| 5,254,294 A | * | 10/1993 | Wunderlich ......... A61K 9/4833 264/4 |
| 5,330,835 A | | 7/1994 | Kikuchi et al. |
| 5,441,660 A | | 8/1995 | Tsaur et al. |
| 6,251,661 B1 | | 6/2001 | Urabe et al. |
| 6,982,095 B2 | | 1/2006 | Asada et al. |
| 8,021,436 B2 | * | 9/2011 | Lant et al. ......................... 8/137 |
| 2001/0021404 A1 | | 9/2001 | Uhlemann et al. |
| 2008/0292692 A1 | | 11/2008 | Pilch et al. |
| 2009/0088362 A1 | * | 4/2009 | Lant et al. .................... 510/276 |
| 2009/0148392 A1 | * | 6/2009 | SenGupta ....................... 424/59 |
| 2011/0028372 A1 | * | 2/2011 | Borup et al. .................. 510/220 |

FOREIGN PATENT DOCUMENTS

| | | | |
|---|---|---|---|
| EP | 1 133 929 A1 | | 9/2001 |
| GB | 1128513 | | 9/1968 |
| JP | 2000-26282 A | | 1/2000 |
| WO | WO91/19487 A1 | * | 12/1991 |
| WO | WO9937746 | * | 7/1999 |

(Continued)

OTHER PUBLICATIONS

International Search Report of PCT/US2012/026043, international filing date of Feb. 22, 2012.

(Continued)

*Primary Examiner* — Vasu Jagannathan
*Assistant Examiner* — Preeti Kumar
(74) *Attorney, Agent, or Firm* — Robert M. Lanning

(57) ABSTRACT

A seamless capsule comprises at least one core and a shell layer. The capsule can further comprise an intermediate layer which surrounds the core(s) and is surrounded by the shell layer. The shell layer comprises a material selected from the group consisting of water-soluble polymers, water-dispersible polymer, hydrogels. The shell layer can further comprise a disintegration aid.

32 Claims, 2 Drawing Sheets

(56) References Cited

FOREIGN PATENT DOCUMENTS

| | | | |
|---|---|---|---|
| WO | WO 01/40430 | A1 | 7/2001 |
| WO | WO 2007/040842 | A1 | 4/2007 |

OTHER PUBLICATIONS

International Search Report of PCT/US2012/026032, international filing date of Feb. 22, 2012.
International Search Report of PCT/US2012/026045, international filing date of Feb. 22, 2012.

* cited by examiner

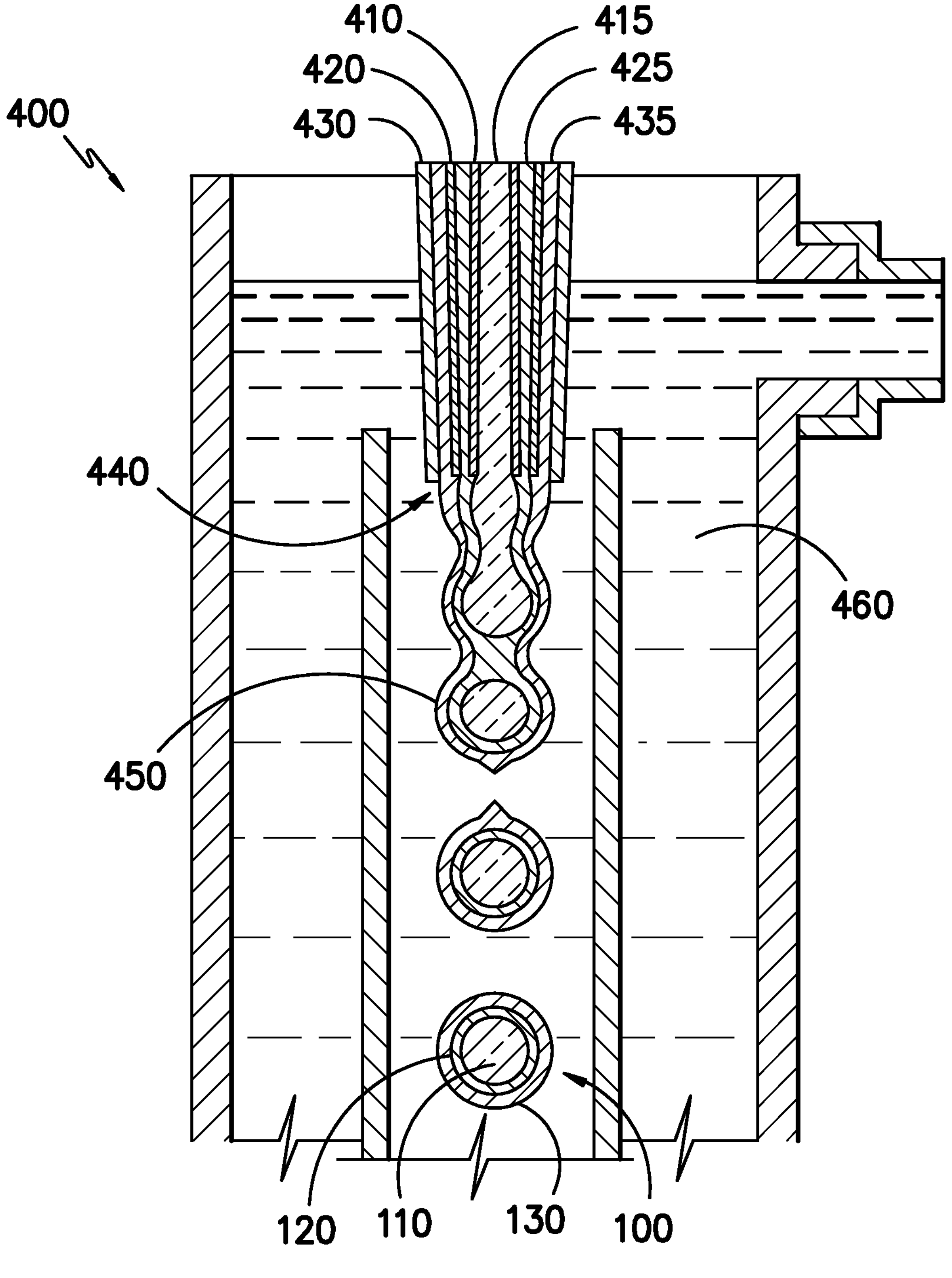
FIG. –4–

CAPSULES AND COMPOSITIONS COMPRISING THE SAME

TECHNICAL FIELD OF THE INVENTION

This application relates to capsules and encapsulated materials that are suitable for use in a variety of applications.

BRIEF SUMMARY OF THE INVENTION

As noted above, the present invention provides capsules (e.g., microcapsules). The capsules generally comprise one or more encapsulated materials and a continuous shell layer surrounding the encapsulated materials. Unlike the capsules that are familiar from pharmaceutical applications, these capsules are not formed by mating two preformed halves. Rather, the shell layer of the capsule is continuous and formed in such a way that it does not have a seam or joint where two halves meet or are joined. The encapsulated materials can be one or more cores, or the encapsulated materials can be a number of discrete cores each surrounded by a continuous intermediate layer. The capsules provided by the invention are believed to be particularly well-suited for the protection of certain components from, for example, deleterious interactions with other components in a system (e.g., cleaning composition, such as a laundry detergent). The capsules are also believed to provide a convenient means by which a bluing agent can be added to a composition, such as a laundry detergent composition, without affecting the overall aesthetics of the composition. In other words, the composition can be provided with virtually any visual appearance because the composition would contain a relatively small number of colored capsules (i.e., capsules containing the bluing agent), whereas the straight addition of the same amount of bluing agent to the composition would result in a composition exhibiting the color of the bluing agent.

In a first embodiment, the invention provides a capsule comprising:

(a) about 1 to about 5 discrete cores, each core independently comprising at least one lipophobic material selected from the group consisting of dyes, pigments, polymeric colorants, optical brighteners, fluorescing dyes, bleaching agents, bleach activators, bleach catalysts, bleach stabilizers, textile hand modifiers, fabric softeners, fabric stiffeners, soil release agents, enzymes, oxidizing agents, antimicrobials, antifungal agents, disinfectants, antioxidants, water softening agents, detergent builders, antiredeposition agents, foam boosters, humectants, water soluble polymers, odor removers, dye-transfer inhibitors, UV absorbers, UV stabilizers, botanic extracts, urea, sequestrants, abrasives, water, and combinations thereof;

(b) a continuous, intermediate layer surrounding each core, the intermediate layer comprising a lipophilic material that is immiscible with or insoluble in aqueous media; and (c) a continuous shell layer surrounding the intermediate layer, the shell layer comprising a material selected from the group consisting of hydrogels, dehydrated hydrogels, water-soluble polymers, water-dispersible polymers, and combinations thereof.

In a second embodiment, the invention provides a capsule comprising:

(a) at least one core; and (b) a continuous shell layer surrounding the core, the shell layer comprising:

(i) a material selected from the group consisting of hydrogels, dehydrated hydrogels, water-soluble polymers, water-dispersible polymers, and combinations thereof; and (ii) a disintegration aid disposed in the shell layer, the disintegration aid exhibiting an absorption of 5 grams or more of solution per gram of disintegration aid as measured in an aqueous solution having an electrical conductivity of about 5 μS/cm or less.

In a third embodiment, the invention provides a capsule comprising:

(a) at least one core, the core comprising a lipophobic material;

(b) a continuous, intermediate layer surrounding each core, the intermediate layer comprising a lipophilic material that is immiscible with or insoluble in aqueous media; and (c) a continuous shell layer surrounding the intermediate layer, the shell layer comprising:

(i) a material selected from the group consisting of hydrogels, dehydrated hydrogels, water-soluble polymers, water-dispersible polymers, and combinations thereof; and (ii) a disintegration aid disposed in the shell layer, the disintegration aid exhibiting an absorption of 5 grams or more of solution per gram of disintegration aid as measured in an aqueous solution having an electrical conductivity of about 5 μS/cm or less.

The invention also provides compositions comprising at least one of the capsules according to the invention. In a specific embodiment, the invention provides a composition comprising at least one surfactant and at least one capsule according to the invention or a plurality of capsules according to the invention. In another embodiment, the invention provides a cleaning composition comprising at least one cleaning agent and at least one capsule according to the invention or a plurality of capsules according to the invention. In yet another embodiment, the invention provides a laundry care composition comprising at least one laundry care ingredient and at least one capsule according to the invention or a plurality of capsules according to the invention.

BRIEF DESCRIPTION OF THE DRAWINGS

FIG. 4 is a cross-section view of a triple nozzle coextrusion apparatus suitable for use in making the capsules according to the invention.

DETAILED DESCRIPTION OF THE INVENTION

As utilized herein, the term "core" refers to a discrete body residing within the interior of a capsule. The core has a distinct boundary separating it from either the surrounding intermediate layer or, in other embodiments, the shell layer. The core can be a solid, a liquid, or both (e.g., a solid dispersed or suspended within a liquid). Furthermore, the core can be a solution containing a solid or a semi-solid dissolved within a suitable solvent (e.g., water, an alcohol, or a mixture thereof).

As utilized herein, the terms "lipophobic" and "lipophilic" are generally used in a relative sense intended to convey the affinity of one component of the capsule (e.g., the core) for another component (e.g., the continuous intermediate layer). Thus, unless specifically noted in the specification, the terms are not intended to indicate that a component exhibits any particular hydrophilic-lipophilic balance value.

Figure 1:
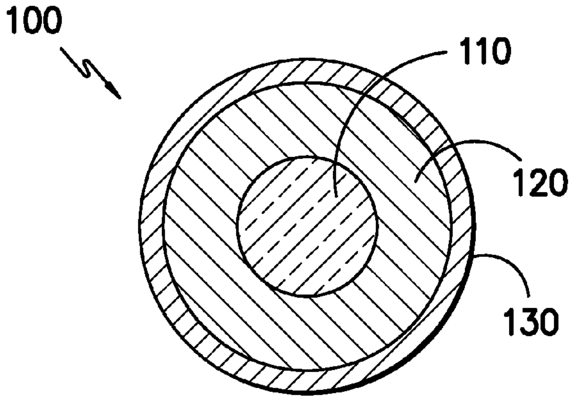
FIG. 1 is a cross-section view of a capsule according to the invention.
Figure 2:
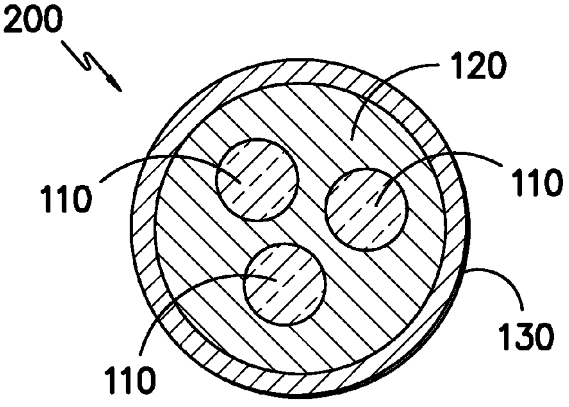
FIG. 2 is a cross-section view of another capsule according to the invention.

In a first embodiment, such as that depicted in FIGS. 1 and 2, the invention provides a capsule 100, 200 comprising a relatively small number of cores 110, a continuous intermediate layer 120 surrounding each core 110, and a continuous shell layer 130 surrounding the intermediate layer 120. In such an embodiment, the capsule can comprise any suitable number of cores. In one particular embodiment, the capsule comprises about 10 cores or less, or about 5 cores or less. In another embodiment, the capsule comprises about 1 to about 5 discrete cores.

In this embodiment, the core comprises a lipophobic material. As utilized in connection with this embodiment, the term "lipophobic" is generally used to denote a material that exhibits a sufficient aversion to the intermediate layer that at least a portion of the material can form a discrete, separate phase when the two are combined and this phase separation remains stable for a substantial period of time (e.g., about 24 hours or more). In a preferred embodiment, the lipophobic material exhibits an octanol-water partition coefficient (log Pow) of less than 6 (e.g., about 5 or less, about 4 or less, about 3 or less, about 2 or less, or about 1 or less). The lipophobic material present in the core can be any suitable lipophobic material. Suitable lipophobic materials include, but are not necessarily limited to, dyes (e.g., acid dyes), pigments, polymeric colorants, optical brighteners, fluorescing dyes, bleaches, textile hand modifiers, fabric softeners, soil release agents, enzymes, oxidizing agents, antimicrobials, antioxidants, water-soluble polymers (e.g., polyethylene glycols, polyvinylpyrrolidone, and cellulose ethers), non-ionic surfactants, anionic surfactants, cationic surfactants, amphoteric surfactants, detergent builders, alkalis, acids, bases, complexing agents, ion-exchangers, bleaching agents, bleach activators, bleach catalysts, bleach stabilizers, enzymes, soil antiredeposition agents, soil repellant agents, soil release agents, foam regulators, corrosion inhibitors, fluorescent whitening agents, fabric softeners, fabric stiffeners, odor removers, dye-transfer inhibitors, polyacrylate dispersants, rheology modifiers, buffers, defoamers, hydrotopes, foam stabilizers, foam boosters, antifungal agents, UV absorbers, botanic extracts, protein hydrolytes, urea, sequestrants, humectants, exfoliants, abrasives, disinfectants, peracids, chelants, UV stabilizers, water, water miscible solvents (e.g., alcohols, DMSO, glycerine, glycol ethers, diethanolamine, other alkanolamines, and amides thereof), and combinations thereof. In certain possibly preferred embodiments, the lipophobic material can be a colorant, such as a dye, pigment, polymeric colorant, or a combination thereof. In certain preferred embodiments, the lipophobic material is a polymeric colorant.

As utilized herein, the term "polymeric colorant" refers to a colorant comprising a chromophore and an oligomeric constituent bound to the chromophore. The oligomeric constituent can be bound to the chromophore via any suitable means, such as a covalent bond, an ionic bond, or suitable electrostatic interaction. The oligomeric constituent can have any suitable formula weight. As utilized herein in reference to the oligomeric constituent, the term "formula weight" refers to the weight (in grams) of the oligomeric constituent per mole of the polymeric colorant. In other words, the "formula weight" of the oligomeric constituent refers to the portion of the polymeric colorant's molecular weight attributable to the oligomeric constituent (the remainder being attributable to the chromophore and any other groups attached thereto). Typically, the oligomeric constituent has a formula weight of about 40 or more. The oligomeric constituent typically has a formula weight of about 3,000 or less. In certain possibly preferred embodiments, the oligomeric constituent has a formula weight of about 40 to about 3,000.

Polymeric colorants suitable for use in the invention include, but are not limited to, those colorants conforming to the structure of Formula (I) or Formula (II) below:

(I)

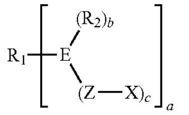

(II)

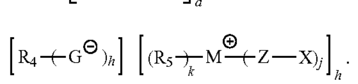

In the structure of Formula (I), $R_1$ or $R_1$-$[E]_a$ is an organic chromophore. Each E is a linking moiety independently selected from the group consisting of nitrogen, oxygen, sulfur, a sulfonyl group, a sulfonate group, a sulfonamide group, and a carboxyl group. Each $R_2$ is independently selected from the group consisting of hydrogen, alkyl groups, alkoxy groups, and aryl groups. The variable a is a positive integer. The variables b and c are independently selected from the group consisting of integers from 0 to 2. If E is nitrogen or a sulfonamide group, the sum of b and c is 2. If E is oxygen, sulfur, a sulfonyl group, a sulfonated group, or a carbonyl, the variable b is 0 and c is 1. Also, the polymeric colorant conforming to the structure of Formula (I) contains at least one —Z—X substituent bound to $R_1$ through a linking moiety E. In other words, if the polymeric colorant contains only one liking moiety E (i.e., a is 1), then at least one —Z—X substituent is bound to the linking moiety E (i.e., c is at least 1). If the polymeric colorant contains multiple linking moieties E (i.e., a is 2 or more), then at least one of the linking moieties has at least one —Z—X substituent thereto (i.e., at least one of the variables c is 1 or greater).

In the structure of Formula (II), $R_4$ or $R_4(G)_h$ is an organic chromophore. G is selected from the group consisting of $SO_3^-$ and $CO_2^-$. Each $R_5$ is independently selected from the group consisting of hydrogen, alkyl groups, and aryl groups; and M is selected from the group consisting of nitrogen atoms and phosphorous atoms. The variable h is an integer from 1 to 4, the variable k is an integer from 0 to 5, and the variable j is an integer from 1 to 6. The sum of k and j is equal to 4 when M is a nitrogen atom and 6 when M is a phosphorous atom.

In each of the structures of Formula (I) or Formula (II), each Z is a divalent organic moiety independently selected from the group consisting of $C_1$-$C_{20}$ alkyl moieties, aryl moieties, alkoxyl moieties, and oligomeric substituents. The oligomeric substituents are selected from the group consisting of (A) divalent oligomeric substituents comprising two or more divalent repeating units independently selected from repeating units conforming to the structure of Formula (III)

(III)

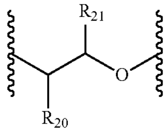

wherein $R_{20}$ and $R_{21}$ are independently selected from the group consisting of hydrogen, alkyl, hydroxyalkyl, aryl, alkoxyalkyl, and aryloxyalkyl; (B) divalent substituents conforming to the structure of Formula (VIII)

(VIII)

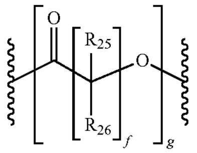

wherein $R_{25}$ and $R_{26}$ are independently selected from the group consisting of hydrogen, hydroxyl, and $C_1$-$C_{10}$ alkyl, f is an integer from 1 to 12, and g is an integer from 1 to 100; and (C) divalent substituents comprising two or more substituents selected from (A) and (B). Also, each X is an end group independently selected from the group consisting of hydrogen, a hydroxyl group, a sulfhydryl group, thiol groups, amine groups, alkyl groups, aryl groups, alkyl ester groups, aryl ester groups, organic sulfonate groups, organic sulfate groups, and amide groups. In certain embodiments, at least one —Z—X substituent of the colorant conforming to the structure of Formula (I) or Formula (II) terminates in a group selected from the group consisting of a hydroxyl group, a sulfhydryl group, thiol groups, primary amine groups, secondary amine groups, primary amide groups, and secondary amide groups. Lastly, in each of the structures of Formula (I) or Formula (II), at least one —Z—X substituent comprises an oligomeric substituent as defined above.

In those embodiments in which the capsule comprises more than one core, the cores can be the same or different. In other words, each core can contain the same component(s), each core can contain different components, or some of the cores can contain the same components and other cores contain different components.

The core(s) can comprise any suitable percentage of the capsule's total volume. In certain embodiments, such as when the shell layer is hydrated (e.g., the shell contains a hydrogel), the core(s) can comprise about 5% to about 95% of the capsule's total volume. In certain other embodiments, such as when the shell layer is dehydrated, the core(s) can comprise about 5% to about 99% of the capsule's total volume. In certain possibly preferred embodiments, the core(s) can comprise about 30% to about 80% of the capsule's total volume.

As noted above, the capsules of the first embodiment comprise a continuous, intermediate layer surrounding each core. The intermediate layer can be any suitable material, but generally the intermediate layer comprises a lipophilic material that is immiscible with or insoluble in aqueous media. As with the term "lipophobic," the term "lipophilic" is used in connection with this embodiment to describe the relative affinity of the core material for the intermediate layer. Thus, the term "lipophilic" is used to describe a material that exhibits a sufficient aversion to the core material that at least a portion of the core material can form a discrete, separate phase when the two are combined and this phase separation remains stable for a substantial period of time (e.g., about 24 hours or more). In a preferred embodiment, the lipophiliic material exhibits an octanol-water partition coefficient of 6 or greater (e.g., about 7 or more, about 8 or more, about 9 or more, or about 10 or more). In certain other embodiments, the lipophilic material exhibits a water solubility of less than about one gram per 100 grams of water at 20° C. and 1 atm pressure.

The intermediate layer can comprise any suitable material exhibiting the properties described above. The intermediate layer can be a solid, a liquid, or both (e.g., a solid dispersed or suspended within a liquid). Furthermore, the intermediate layer can be a solution containing a solid dissolved within a suitable solvent. Lipophilic materials suitable for use as the intermediate layer include, but are not limited to, vegetable oils (e.g., corn oil), vegetable fats, animal oils, animal fats, mineral oil, paraffinic oils, parrafinic waxes, silicone oils, and mixtures thereof. In certain possibly preferred embodiments, the intermediate layer comprises a vegetable oil (e.g., corn oil) or a silicone oil.

The intermediate layer can comprise any suitable percentage of the capsule's total volume. In certain embodiments, the intermediate layer can comprise about 2% to about 90% of the capsule's total volume. In certain preferred embodiments, the intermediate layer can comprise about 4% to about 50% of the capsule's total volume or about 6% to about 30% of the capsule's total volume.

While the lipophobic material of the core and the lipophilic material of the intermediate layer can be selected to yield capsules in which the core(s) will remain stable for an extended period of time, it may be desirable to increase the stability of the core(s) by incorporating additional components into the intermediate layer. For example, the stability of the cores can be increased by dispersing or suspending a hydrophobic, particulate material in the intermediate layer. In such an embodiment, the hydrophobic, particulate material can be any suitable particulate material that can be stably dispersed or suspended in the intermediate layer. Suitable hydrophobic, particulate materials include, but are not limited to, hydrophobic silica (e.g., hydrophobic fumed silica, hydrophobic precipitated silica, and mixtures thereof), hydrophobic clays, hydrophobic sands, hydrophobic minerals, hydrophobic carbonaceous particles, and combinations thereof. While not wishing to be bound to any particular theory, it is believed that such hydrophobic, particulate materials act as barriers that help to contain the cores and block the cores from contacting the shell layer, which can result in the rupture of the shell layer and capsule.

If a hydrophobic particulate material is used, the hydrophobic particles can be present in the intermediate layer in any suitable amount. Generally, the hydrophobic particles are added to the intermediate layer in an amount sufficient to appreciably increase the stability of the core(s) and the capsule. In those embodiments in which the intermediate layer contains a hydrophobic particulate material, the hydrophobic particulate material can be present in the intermediate layer in an amount of about 45% or less (e.g., about 25% or less, about 20% or less, about 15% or less, about 10% or less, or about 5% or less), based on the total weight of the intermediate layer. In those embodiments in which the intermediate layer contains a hydrophobic particulate material, the hydrophobic material can be present in the intermediate layer in an amount of about 0.1 wt. % or more (e.g., about 0.2 wt. % or more, about 0.3 wt. % or more, about 0.4 wt. % or more, about 0.5 wt. % or more, about 0.6 wt. % or more, about 0.7 wt. % or more, about 0.8 wt. % or more, about 0.9 wt. % or more, or about 1 wt. % or more).

In addition to the lipophilic material and the hydrophobic particulate material described above, the intermediate layer can comprise additional components. Due to the lipophilic nature of the materials contained in the intermediate layer, the suitable additional components typically are those that can be dissolved or dispersed in the lipophilic material described above. Suitable examples include, but are not limited to, hydrophobic/lipophilic colorants (e.g., pigments, dyes, polymeric colorants), hydrophobic/lipophilic perfumes, hydrophobic/lipophilic fragrances, hydrophobic/lipophilic antifoaming agents, hydrophobic/lipophilic suds depressants, opacifiers, hydrophobic/lipophilic fluorescent whitening agents, hydrophobic/lipophilic fabric softeners, hydrophobic/lipophilic antistatic agents, other oils (e.g., eucalyptus oils or pine oils), and combinations thereof.

In this first embodiment, the capsule comprises a shell layer surrounding the intermediate layer. The shell layer can be made from any suitable material that forms a shell of sufficient durability to encapsulate the core and intermediate layer and is stable for an extended period of time when in contact with the intermediate layer. Thus, in this embodiment, the shell layer typically is not comprised of a material that exhibits an appreciable solubility in the lipophilic material present in the intermediate layer. Accordingly, the shell layer typically comprises a material that is water-soluble, water-dispersible, or contains a significant amount of water (e.g., a hydrogel). Suitable materials for the shell layer include, but are not limited to, hydrogels, dehydrated hydrogels, water-soluble polymers, water-dispersible polymers, and combinations thereof. The hydrogels can be formed using any suitable gelling agent. Suitable gelling agents include, but are not necessarily limited to, polysaccharides, gelatin, alginates, agarose, carrageenans (e.g., κ-carrageenan), pectin, gellan, collagen, and mixtures thereof. In certain possibly preferred embodiments, the gelling agent is agar. In certain embodiments, the water-soluble polymer and water-dispersable polymer can be selected from the group consisting of acrylates, polyhydric alcohols, polysaccharides and modified versions thereof, polyvinyl acetate, polyvinyl pyrrolidone, methyl cellulose, carboxymethyl cellulose, hydroxyethyl cellulose, hydroxypropyl cellulose, hydroxybutyl cellulose, hydroxylpropyl methylcellulose, acrylamides, acrylates, chitosan, polyethylene glycols, locust bean gum, xanthan gum, guar gum, pectin, carrageenans, alginates, agarose, gelatin, and mixtures thereof. In certain possibly preferred embodiments, the shell layer comprises a water-soluble polymer, and the water-soluble polymer is a polyvinyl alcohol. As noted above, when the shell material is a water-soluble or water-dispersable polymer, the shell can also contain a gelling agent, such as any of the gelling agents listed above.

In certain embodiments, such as when the shell layer comprises a hydrogel or dehydrated hydrogel, the shell layer can further comprise a crosslinking agent. The function of the crosslinking agent is to cause the gelling agent to gel, thereby yielding a hydrogel that is capable of forming the shell layer of the capsule. Suitable cross-linking agents include, but are not limited to, boric acid, caustic, formaldehyde, glutaraldehyde, acetaldehyde, polyaldehydes, zirconium salts (e.g., zirconium chloride, zirconium tetrachloride, zirconyl chloride), salts containing di or trivalent counter ions (e.g., calcium salts), diisocyanates, triols, epichlorohydrin, dextranaldehydes, dialdehydes, tripolyphosphates, carbodiimides, polyepoxides, isocyanates and combinations thereof.

The capsules of the invention are generally designed to be used in a composition (e.g., cleaning composition or laundry detergent composition) that is added to or diluted with an appreciable amount of water during use. With such addition or dilution, the water can dissolve or otherwise disintegrate the shell layer thereby releasing the contents of the capsule (e.g., core(s) and, if present, intermediate layer). While the material used in the shell layer can be selected so that it is readily soluble in water, it has been found that the disintegration of the shell layer can, under certain conditions, proceed relatively slowly leading to a delayed release of the contents of the capsule. Furthermore, in the case of a capsule having a hydrogel shell, the shell layer will not dissolve or disintegrate to release the capsule contents because, once the hydrogel shell has formed, it is stable in aqueous environments. Accordingly, in certain embodiments, it may be desirable to incorporate into the shell layer a material that promotes the disintegration of the shell layer. Such a material will be referred to herein as a "disintegration aid." The disintegration aid can be any suitable material that promotes a more rapid disintegration of the shell layer. The disintegration aid can function to promote or accelerate the disintegration of the shell layer by any suitable mechanism. For example, the disintegration aid can be a material that dissolves under certain conditions, which would leave voids or weak spots in the shell layer that allow the capsule to rupture more easily. The disintegration aid can also be a material that expands or swells under certain conditions, which would exert forces on the shell layer as it expands and cause the shell layer to rupture.

In certain embodiments, the disintegration aid exhibits an absorption of 5 grams or more of solution per gram of disintegration aid as measured in an aqueous solution having an electrical conductivity of about 5 μS/cm or less. In certain other embodiments, the disintegration aid exhibits an absorption of about 10 grams or more, about 20 grams or more, about 30 grams or more, about 40 grams or more, about 50 grams or more, about 60 grams or more, about 70 grams or more, or about 75 grams or more of solution per gram of disintegration aid as measured in an aqueous solution having an electrical conductivity of about 5 μS/cm or less. Suitable disintegration aids include, but are not limited to, superabsorbent polymers, swellable clays, xerogels, and combinations thereof. In those embodiments in which the disintegration aid is a superabsorbent polymer, the superabsorbent polymer can be added to the shell layer composition as particles of the final, crosslinked polymer or the superabsorbent polymer can be in situ formed in the shell by adding an polymer precursor that is then crosslinked during shell formation.

If the disintegration aid is used, the disintegration aid can be present in the shell layer in any suitable amount. Generally, the disintegration aid is added to the shell layer in an amount sufficient to appreciably accelerate the disintegration of the shell layer and release of the contents of the capsule. For example, the disintegration aid can be present in the shell layer in an amount of about 0.1 wt. % or more, about 0.2 wt. % or more, about 0.3 wt. % or more, 0.4 wt. % or more, or about 0.5 wt. % or more based on the total weight of the shell layer. Further, the disintegration aid can be present in the shell layer in an amount of about 85 wt. % or less, about 80 wt. % or less, about 75 wt. % or less, about 70 wt. % or less, about 65 wt. % or less, about 60 wt. % or less, about 55 wt. % or less, about 50 wt. % or less, about 45 wt. % or less, about 40 wt. % or less, about 35 wt. % or less, or about 30 wt. % or less based on the total weight of the shell layer. In certain embodiments, the disintegration aid is present in the shell layer in an amount of about 0.1 wt. % to about 80 wt. % based on the total weight of the shell layer. In certain other embodiments, such as when the disintegration aid is a superabsorbent polymer incorporated into the shell layer in particulate form, the disintegration aid can be present in the shell layer in an amount of about 0.5 wt. % to about 10 wt. % based on the total weight of the shell layer.

In addition to the polymers and the disintegration aid described above, the shell layer can comprise additional components. For example, in certain embodiments it may be desirable for the capsule's shell layer to be opaque or at least relatively translucent. In order to produce such capsules, a suitable opacifier can be incorporated into the shell layer by, for example, adding the opacifier to the shell layer composition.

Figure 3:
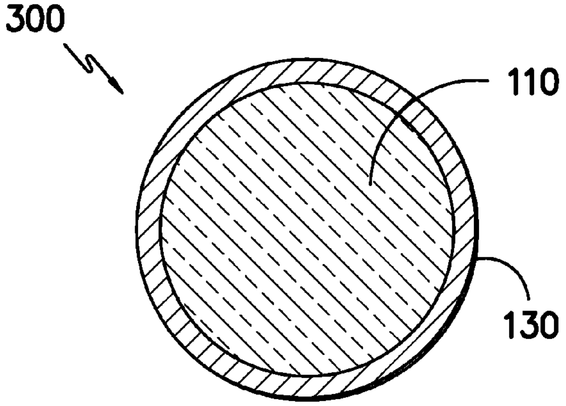
FIG. 3 is a cross-section view of another capsule according to the invention.

In a second embodiment, such as that depicted in FIG. 3, the invention provides a capsule 300 comprising at least one core 110 and a continuous shell layer 130 surrounding the core(s) 110. In such an embodiment, the core can be any suitable material, including those described above for the core or the intermediate layer of the first capsule embodiment of the invention. Preferably, in such an embodiment of the invention, the core is a solid, semi-solid, or a lipophilic material such as those described above for the intermediate layer of the first capsule embodiment of the invention. The shell layer comprises a material for forming the shell and a disintegration aid disposed in the shell layer. The material for forming the shell and the disintegration aid used in such shell layer can be any suitable materials, including those described above for the first capsule embodiment of the invention.

In a third embodiment, the invention provides a capsule comprising at least one core, a continuous, intermediate layer surrounding the core, and a continuous shell layer surrounding the intermediate layer. In such an embodiment, the core can be any suitable material, but generally the core comprises a lipophobic material such as those described above for the first capsule embodiment of the invention. The intermediate layer can be any suitable material, but generally the intermediate layer comprises a lipophobic material, such as those described above for the first capsule embodiment of the invention. The shell layer comprises a material for forming the shell and a disintegration aid disposed in the shell layer. The material for forming the shell and the disintegration aid used in such shell layer can be any suitable materials, including those described above for the first capsule embodiment of the invention.

The capsules of the invention can have any suitable dimensions. For example, the capsules of the invention typically have a diameter of about 10 mm or less, about 9 mm or less, about 8 mm or less, about 7 mm or less, about 6 mm or less, or about 5 mm or less. In certain possibly preferred embodiments, the capsules of the invention can have a diameter of about 0.05 mm to about 10 mm (e.g., about 0.05 mm to about 9 mm, about 0.05 mm to about 8 mm, about 0.05 mm to about 7 mm, about 0.05 mm to about 6 mm, about 0.05 mm to about 5 mm, about 0.06 mm to about 5 mm, about 0.07 mm to about 5 mm, about 0.08 mm to about 5 mm, about 0.09 mm to about 5 mm, or about 0.1 mm to about 5 mm).

The capsules of the invention can be made by any method known in the art to be suitable for producing microencapsulated materials. For example, the capsules can be made by centrifugal coextrusion encapsulation processes, jet cutting encapsulation processes, vibrating nozzle encapsulation process, and multiple nozzle coextrusion encapsulation processes. In certain possibly preferred embodiments, the capsules of the invention are made by a triple nozzle coextrusion encapsulation process. A suitable triple nozzle coextrusion process and apparatus are described, for example, in U.S. Pat. No. 5,330,835 (Kikuchi et al.), the disclosure of which is hereby incorporated by reference.

As noted above, FIG. 4 depicts a triple nozzle coextrusion apparatus suitable for use in producing capsules according to the invention. The apparatus 400 comprises a first nozzle 410, a second nozzle 420, and a third nozzle 430. The first nozzle 410, second nozzle 420, and third nozzle 430 are each positioned in an concentric arrangement. The first nozzle 410 has a smaller diameter than the second nozzle 420 and is positioned within the second nozzle 420. The second nozzle 420 has a smaller diameter than the third nozzle 420 and is positioned within the third nozzle 430. The first nozzle 410 has an interior passage (not marked) that is adapted to convey the material for the core(s) to the nozzle tip 440. The second nozzle 420 has an interior passage (not marked) that is adapted to convey the material for the intermediate layer to the nozzle tip 440. The third nozzle 430 has an interior passage (not marked) that is adapted to convey the material for the shell layer to the nozzle tip 440.

In operation, the components for forming the core(s) 415, the intermediate layer 425, and the shell layer 435 are each fed to the first nozzle 410, second nozzle 420, and third nozzle 430, respectively, in a liquid state so that the components can be extruded through each nozzle to form the capsule. If the component(s) for forming either the core(s), the intermediate layer, or the shell layer are solid at room temperature, the component(s) can heated to a temperature sufficient to melt the component(s) and yield a flowable liquid that can be extruded through the nozzle. Alternatively, these component(s) can be dissolved in a suitable solvent or suspended in a suitable medium.

As the components for forming the core(s) 415, the intermediate layer 425, and the shell layer 435 each exit the nozzle tip 440, the component(s) for the shell layer 435 envelops the component(s) for the intermediate layer 425, and the component(s) for the intermediate layer 425 envelops the component(s) for the core(s) 415. The result is a capsule intermediate 450 that then passes through a cooling solution 460, which cools the intermediate and allows the shell layer to solidify to the desired degree. The end result is a capsule 100 having at least one core 110 surrounded by a continuous, intermediate layer 120 and a shell layer 130 surrounding the intermediate layer 120. The cooling solution 460 can be circulated so that it flows past the nozzle tip 440 in the same direction as the emerging capsule intermediate 450.

In the above-described process, the flow rates of the components for the core(s) 415, the intermediate layer 425, and the shell layer 435 can each be individually controlled to adjust the size of the capsules and the percentage of capsule mass or volume contributed by the core, intermediate layer, and shell layer. For example, the flow rates can be adjusted so as to produce capsules containing multiple cores. Furthermore, the flow rate of the cooling solution can be varied to control the thickness of the shell layer. In general and with all other variables being the same, higher flow rates of the cooling solution will produce capsules having thinner shell layers.

As noted above, the capsules of the invention are believed to be particularly well-suited for use in applications in which the capsules, or a composition containing the capsules, are added to or diluted with water. With such addition to or dilution with water, the shell layer of the capsules disintegrates and/or dissolves, which releases the contents of the capsule (e.g., core(s) and, if present, intermediate layer). Thus, the capsules of the invention are believed to be well-suited for use in a variety of compositions that are typically used in conjunction with water, such as cleaning compositions (e.g., household cleaning compositions, dish soaps, dishwashing detergent compositions, and laundry detergent compositions), personal care compositions (e.g., liquid hand soaps, liquid body washes, and shampoos), pet care compositions (e.g., liquid pet washes and liquid pet shampoos), and automotive care compositions (e.g., automotive cleaners and automotive degreasers).

While the liquid compositions mentioned above typically contain water, it is believed that the capsules of the invention can remain stable in these compositions for extended periods of time. For example, it has been found that capsules of the invention having a hydrogel shell can remain stable in water for extended periods of time. Therefore, it is believed that such capsules will, under standard or normal conditions, also remain stable in the aqueous compositions mentioned above. This extended stability of the capsule provides a means to protect the capsule's contents from the harsh conditions present in many of the above-mentioned compositions. Furthermore, the capsules generally will not rupture and release their contents until the capsules (or a composition containing the capsules) are exposed to a substantial change in conditions, such as high temperatures or aggressive mechanical forces (e.g., aggressive agitation).

The above-mentioned compositions also typically contain relatively large amounts of ionic surfactants (e.g., anionic surfactants), and the presence of these ionic compounds produces a composition exhibiting a relatively high ionic strength. When such compositions are added to or diluted with water, the ionic strength of the resulting mixture (i.e., the composition plus water) will be appreciably lower than that of the composition itself. This change in ionic strength between the composition and the diluted composition can also provide a means by which the capsule's rupture can be triggered. For example, the capsule can be designed so that the shell layer (e.g., a hydrogel-based shell layer) contains a disintegration aid whose swelling is inhibited in high ionic strength environments. One example of such a disintegration aid would be a superabsorbent polymer. When a composition containing such capsules is added to or diluted with water, the ionic strength of the resulting mixture (i.e., the composition plus water) will be appreciably lower than that of the composition itself. In this lower ionic strength environment, the superabsorbent polymer readily swells, causing the shell layer to disintegrate and releases the contents of the capsule. Indeed, this very behavior is observed when such capsules of the invention are added to, for example, a liquid laundry detergent composition. The capsules are stable in the composition for an extended period of time, with none or only a very small number of the capsules rupturing in the detergent composition. However, when the laundry detergent composition is added to water under normal washing conditions, the capsules rupture and release their contents (e.g., the core(s) and, if present, the intermediate layer). This behavior is believed to make the capsules of the invention particularly well-suited for the delivery of components that would typically be degraded or otherwise unstable if added directly to the composition.

Thus, the invention also provides compositions comprising the capsules of the invention. In one embodiment, the invention provides a composition comprising at least one surfactant and at least one capsule according to the invention or a plurality of capsules according to the invention. The surfactant used in such embodiment can be any suitable surfactant, such as those typically used in cleaning compositions (e.g., liquid laundry detergents, fabric softeners, dish washing detergents), personal care compositions (e.g., liquid hand soaps, liquid body washes, and shampoos), pet care compositions, and automotive care compositions. In this embodiment, the composition can be provided in any suitable form (e.g., solid or liquid), with liquid compositions being preferred. In such a liquid composition, the surfactant and capsule(s) of the invention can be incorporated into any suitable liquid medium or carrier, with aqueous media or carriers being preferred.

In another embodiment, the invention provides a cleaning composition comprising at least one cleaning agent and at least one capsule according to the invention or a plurality of capsules according to the invention. In this embodiment, the cleaning agent can be any suitable agent or compound typically used in cleaning compositions (e.g., household cleaning compositions). Suitable cleaning agents include, but are not limited to, surfactants (e.g., detersive surfactants), disinfectants, degreasers, bleaches, and combinations thereof.

In view of their properties and performance, the capsules of the invention are believed to be particularly well-suited for use in laundry care compositions. Thus, in yet another embodiment, the invention provides a laundry care composition comprising at least one laundry care ingredient and at least one capsule according to the invention or a plurality of capsules according to the invention. The following paragraphs describe in detail such laundry care compositions and components suitable for use in the same.

As used herein, the term "laundry care composition" includes, unless otherwise indicated, granular, powder, liquid, gel, paste, bar form and/or flake type washing agents and/or fabric treatment compositions. As used herein, the term "fabric treatment composition" includes, unless otherwise indicated, fabric softening compositions, fabric enhancing compositions, fabric freshening compositions and combinations thereof. Such compositions can be, but need not be, rinse added compositions.

The capsules described in the present specification can be incorporated into a laundry care composition including, but not limited to, laundry detergents and fabric care compositions. Such compositions comprise a plurality of said capsules and a laundry care ingredient. The laundry care compositions including laundry detergents can be in solid or liquid form, including a gel form. The laundry detergent composition comprises a surfactant in an amount sufficient to provide desired cleaning properties.

The capsules can be present in the laundry detergent composition in an amount from about 0.0001% to about 10% by weight of the composition, more preferably from about 0.001% to about 5% by weight of the composition, and even more preferably from about 0.01% to about 1% by weight of the composition.

The laundry detergent composition comprises a surfactant in an amount sufficient to provide desired cleaning properties. In one embodiment, the laundry detergent composition comprises, by weight, from about 5% to about 90% of the surfactant, and more specifically from about 5% to about 70% of the surfactant, and even more specifically from about 5% to about 40%. The surfactant can comprise anionic, nonionic, cationic, zwitterionic and/or amphoteric surfactants. In a more specific embodiment, the detergent composition comprises anionic surfactant, nonionic surfactant, or mixtures thereof.

Suitable anionic surfactants useful herein can comprise any of the conventional anionic surfactant types typically used in liquid detergent products. These include the alkyl benzene sulfonic acids and their salts as well as alkoxylated or non-alkoxylated alkyl sulfate materials.

Exemplary anionic surfactants are the alkali metal salts of $C_{10}$-$C_{16}$ alkyl benzene sulfonic acids, preferably $C_{11}$-$C_{14}$ alkyl benzene sulfonic acids. Preferably the alkyl group is linear and such linear alkyl benzene sulfonates are known as "LAS". Alkyl benzene sulfonates, and particularly LAS, are well known in the art. Such surfactants and their preparation are described for example in U.S. Pat. Nos. 2,220,099 and 2,477,383. Especially preferred are the sodium and potassium linear straight chain alkylbenzene sulfonates in which the average number of carbon atoms in the alkyl group is from about 11 to 14. Sodium $C_{11}$-$C_{14}$, e.g., $C_{12}$, LAS is a specific example of such surfactants.

Another exemplary type of anionic surfactant comprises ethoxylated alkyl sulfate surfactants. Such materials, also known as alkyl ether sulfates or alkyl polyethoxylate sulfates, are those which correspond to the formula: $R'—O—(C_2H_4O)_n—SO_3M$ wherein R' is a $C_8$-$C_{20}$ alkyl group, n is from about 1 to 20, and M is a salt-forming cation. In a specific embodiment, R' is $C_{10}$-$C_{18}$ alkyl, n is from about 1 to 15, and M is sodium, potassium, ammonium, alkylammonium, or alkanolammonium. In more specific embodiments, R' is a $C_{12}$-$C_{16}$ alkyl, n is from about 1 to 6, and M is sodium.

The alkyl ether sulfates will generally be used in the form of mixtures comprising varying R' chain lengths and varying degrees of ethoxylation. Frequently such mixtures will inevitably also contain some non-ethoxylated alkyl sulfate materials, i.e., surfactants of the above ethoxylated alkyl sulfate formula wherein n=0. Non-ethoxylated alkyl sulfates can also be added separately to the compositions of this invention and used as or in any anionic surfactant component which may be present. Specific examples of non-alkoxylated, e.g., non-ethoxylated, alkyl ether sulfate surfactants are those produced by the sulfation of higher $C_8$-$C_{20}$ fatty alcohols. Conventional primary alkyl sulfate surfactants have the general formula: $ROSO_3^-M^+$ wherein R is typically a linear $C_8$-$C_{20}$ hydrocarbyl group, which can be straight chain or branched chain, and M is a water-solubilizing cation. In specific embodiments, R is a $C_{10}$-$C_{15}$ alkyl, and M is alkali metal, more specifically R is $C_{12}$-$C_{14}$ and M is sodium.

Specific, non-limiting examples of anionic surfactants useful herein include: a) $C_{11}$-$C_{18}$ alkyl benzene sulfonates (LAS); b) $C_{10}$-$C_{20}$ primary, branched-chain and random alkyl sulfates (AS); c) $C_{10}$-$C_{18}$ secondary (2,3)alkyl sulfates having formulae (I) and (II): wherein M in formulae (I) and (II) is hydrogen or a cation which provides charge neutrality, and all M units, whether associated with a surfactant or adjunct ingredient, can either be a hydrogen atom or a cation depending upon the form isolated by the artisan or the relative pH of the system wherein the compound is used, with non-limiting examples of preferred cations including sodium, potassium, ammonium, and mixtures thereof, and x is an integer of at least about 7, preferably at least about 9, and y is an integer of at least 8, preferably at least about 9; d) $C_{10}$-$C_{18}$ alkyl alkoxy sulfates ($AE_xS$) wherein preferably x is from 1-30; e) $C_{10}$-$C_{18}$ alkyl alkoxy carboxylates preferably comprising 1-5 ethoxy units; f) mid-chain branched alkyl sulfates as discussed in U.S. Pat. No. 6,020,303 and U.S. Pat. No. 6,060,443; g) mid-chain branched alkyl alkoxy sulfates as discussed in U.S. Pat. No. 6,008,181 and U.S. Pat. No. 6,020,303; h) modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; i) methyl ester sulfonate (MES); and j) alpha-olefin sulfonate (AOS).

Suitable nonionic surfactants useful herein can comprise any of the conventional nonionic surfactant types typically used in liquid detergent products. These include alkoxylated fatty alcohols and amine oxide surfactants. Preferred for use in the liquid detergent products herein are those nonionic surfactants which are normally liquid.

Suitable nonionic surfactants for use herein include the alcohol alkoxylate nonionic surfactants. Alcohol alkoxylates are materials which correspond to the general formula: $R^1(C_mH_{2m}O)_nOH$ wherein $R^1$ is a $C_8$-$C_{16}$ alkyl group, m is from 2 to 4, and n ranges from about 2 to 12. Preferably $R^1$ is an alkyl group, which can be primary or secondary, that comprises from about 9 to 15 carbon atoms, more preferably from about 10 to 14 carbon atoms. In one embodiment, the alkoxylated fatty alcohols will also be ethoxylated materials that contain from about 2 to 12 ethylene oxide moieties per molecule, more preferably from about 3 to 10 ethylene oxide moieties per molecule.

The alkoxylated fatty alcohol materials useful in the liquid detergent compositions herein will frequently have a hydrophilic-lipophilic balance (HLB) which ranges from about 3 to 17. More preferably, the HLB of this material will range from about 6 to 15, most preferably from about 8 to 15. Alkoxylated fatty alcohol nonionic surfactants have been marketed under the tradenames Neodol and Dobanol by the Shell Chemical Company.

Another suitable type of nonionic surfactant useful herein comprises the amine oxide surfactants. Amine oxides are materials which are often referred to in the art as "semi-polar" nonionics. Amine oxides have the formula: $R(EO)_x(PO)_y(BO)_zN(O)(CH_2R')_2.qH2O$. In this formula, R is a relatively long-chain hydrocarbyl moiety which can be saturated or unsaturated, linear or branched, and can contain from 8 to 20, preferably from 10 to 16 carbon atoms, and is more preferably $C_{12}$-$C_{16}$ primary alkyl. R' is a short-chain moiety, preferably selected from hydrogen, methyl and $—CH_2OH$. When x+y+z is different from 0, EO is ethyleneoxy, PO is propyleneneoxy and BO is butyleneoxy. Amine oxide surfactants are illustrated by $C_{12}$-$C_{14}$ alkyldimethyl amine oxide.

Non-limiting examples of nonionic surfactants include: a) $C_{12}$-$C_{18}$ alkyl ethoxylates, such as, NEODOL® nonionic surfactants from Shell; b) $C_6$-$C_{12}$ alkyl phenol alkoxylates wherein the alkoxylate units are a mixture of ethyleneoxy and propyleneoxy units; c) $C_{12}$-$C_{18}$ alcohol and $C_6$-$C_{12}$ alkyl phenol condensates with ethylene oxide/propylene oxide block polymers such as Pluronic® from BASF; d) $C_{14}$-$C_{22}$ mid-chain branched alcohols, BA, as discussed in U.S. Pat. No. 6,150,322; e) $C_{14}$-$C_{22}$ mid-chain branched alkyl alkoxylates, $BAE_x$, wherein x is from 1-30, as discussed in U.S. Pat. No. 6,153,577, U.S. Pat. No. 6,020,303 and U.S. Pat. No. 6,093,856; f) Alkylpolysaccharides as discussed in U.S. Pat. No. 4,565,647 to Llenado, issued Jan. 26, 1986; specifically alkylpolyglycosides as discussed in U.S. Pat. No. 4,483,780 and U.S. Pat. No. 4,483,779; g) Polyhydroxy fatty acid amides as discussed in U.S. Pat. No. 5,332,528, WO 92/06162, WO 93/19146, WO 93/19038, and WO 94/09099; and h) ether capped poly(oxyalkylated) alcohol surfactants as discussed in U.S. Pat. No. 6,482,994 and WO 01/42408.

In the laundry detergent compositions herein, the detersive surfactant component can comprise combinations of anionic and nonionic surfactant materials. When this is the case, the weight ratio of anionic to nonionic will typically range from 10:90 to 90:10, more typically from 30:70 to 70:30.

Cationic surfactants are well known in the art and non-limiting examples of these include quaternary ammonium surfactants, which can have up to 26 carbon atoms. Additional examples include a) alkoxylate quaternary ammonium (AQA) surfactants as discussed in U.S. Pat. No. 6,136,769; b) dimethyl hydroxyethyl quaternary ammonium as discussed in U.S. Pat. No. 6,004,922; c) polyamine cationic surfactants as discussed in WO 98/35002, WO 98/35003, WO 98/35004, WO 98/35005, and WO 98/35006; d) cationic ester surfactants as discussed in U.S. Pat. Nos. 4,228,042, 4,239,660 4,260,529 and U.S. Pat. No. 6,022,844; and e) amino surfactants as discussed in U.S. Pat. No. 6,221,825 and WO 00/47708, specifically amido propyldimethyl amine (APA).

Non-limiting examples of zwitterionic surfactants include derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants; betaine, including alkyl dimethyl betaine and cocodimethyl amidopropyl betaine, $C_8$ to $C_{18}$ (preferably $C_{12}$ to $C_{18}$) amine oxides and sulfo and hydroxy betaines, such as N-alkyl-N,N-dimethylammino-1-propane sulfonate where the alkyl group can be $C_8$ to $C_{18}$, preferably $C_{10}$ to $C_{14}$.

Non-limiting examples of ampholytic surfactants include aliphatic derivatives of secondary or tertiary amines, or aliphatic derivatives of heterocyclic secondary and tertiary amines in which the aliphatic radical can be straight- or branched-chain. One of the aliphatic substituents comprises at least about 8 carbon atoms, typically from about 8 to about 18 carbon atoms, and at least one comprises an anionic water-solubilizing group, e.g. carboxy, sulfonate, sulfate. See U.S. Pat. No. 3,929,678 to Laughlin et al., issued Dec. 30, 1975 at column 19, lines 18-35, for examples of ampholytic surfactants.

As noted, the compositions can be in the form of a solid, either in tablet or particulate form, including, but not limited to, particles, flakes, or the like, or the compositions can be in the form of a liquid. The liquid detergent compositions comprise an aqueous, non-surface active liquid carrier. Generally, the amount of the aqueous, non-surface active liquid carrier employed in the compositions herein will be effective to solubilize, suspend or disperse the composition components. For example, the compositions can comprise, by weight, from about 5% to about 90%, more specifically from about 10% to about 70%, and even more specifically from about 20% to about 70% of the aqueous, non-surface active liquid carrier.

The most cost effective type of aqueous, non-surface active liquid carrier is, of course, water itself. Accordingly, the aqueous, non-surface active liquid carrier component will generally be mostly, if not completely, comprised of water. While other types of water-miscible liquids, such alkanols, diols, other polyols, ethers, amines, and the like, have been conventionally been added to liquid detergent compositions as co-solvents or stabilizers, for purposes of the present invention, the utilization of such water-miscible liquids should be minimized to hold down composition cost. Accordingly, the aqueous liquid carrier component of the liquid detergent products herein will generally comprise water present in concentrations ranging from about 5% to about 90%, more preferably from about 20% to about 70%, by weight of the composition.

Detergent compositions can also contain bleaching agents. Suitable bleaching agents include, for example, hydrogen peroxide sources, such as those described in detail in the herein incorporated Kirk Othmer's Encyclopedia of Chemical Technology, 4th Ed (1992, John Wiley & Sons), Vol. 4, pp. 271-300 "Bleaching Agents (Survey)." These hydrogen peroxide sources include the various forms of sodium perborate and sodium percarbonate, including various coated and modified forms of these compounds.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Also useful are sources of available oxygen such as persulfate bleach (e.g., OXONE, manufactured by DuPont). Sodium perborate monohydrate and sodium percarbonate are particularly preferred. Mixtures of any convenient hydrogen peroxide sources can also be used.

A suitable percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with a silicate, borate or water-soluble surfactants. Percarbonate is available from various commercial sources such as FMC, Solvay and Tokai Denka.

Compositions of the present invention can also comprise as the bleaching agent a chlorine-type bleaching material. Such agents are well known in the art, and include for example sodium dichloroisocyanurate ("NaDCC"). However, chlorine-type bleaches are less preferred for compositions which comprise enzymes.

(a) Bleach Activators—

Preferably, the peroxygen bleach component in the composition is formulated with an activator (peracid precursor). The activator is present at levels of from about 0.01%, preferably from about 0.5%, more preferably from about 1% to about 15%, preferably to about 10%, more preferably to about 8%, by weight of the composition. A bleach activator as used herein is any compound which, when used in conjunction with a hydrogen peroxide, source leads to the in situ production of the peracid corresponding to the bleach activator. Various non-limiting examples of activators are disclosed in U.S. Pat. Nos. 5,576,282; 4,915,854 and 4,412,934. See also U.S. Pat. No. 4,634,551 for other typical bleaches and activators useful herein.

Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$—OBS), benzoylvalerolactam (BZVL), octanoyloxybenzenesulphonate ($C_8$—OBS), perhydrolyzable esters and mixtures thereof, most preferably benzoylcaprolactam and benzoylvalerolactam. Particularly preferred bleach activators in the pH range from about 8 to about 11 are those selected having an OBS or VL leaving group.

Preferred hydrophobic bleach activators include, but are not limited to, nonanoyloxybenzenesulphonate (NOBS);

4-[N-(nonanoyl)amino hexanoyloxy]-benzene sulfonate sodium salt (NACA-OBS), an example of which is described in U.S. Pat. No. 5,523,434; dodecanoyloxybenzenesulphonate (LOBS or $C_{12}$—OBS); 10-undecenoyloxybenzenesulfonate (UDOBS or $C_{11}$—OBS with unsaturation in the 10 position); and decanoyloxybenzoic acid (DOBA).

Preferred bleach activators are those described in U.S. Pat. No. 5,998,350 to Burns et al.; U.S. Pat. No. 5,698,504 to Christie et al.; U.S. Pat. No. 5,695,679 to Christie et al.; U.S. Pat. No. 5,686,401 to Willey et al.; U.S. Pat. No. 5,686,014 to Hartshorn et al.; U.S. Pat. No. 5,405,412 to Willey et al.; U.S. Pat. No. 5,405,413 to Willey et al.; U.S. Pat. No. 5,130,045 to Mitchel et al.; and U.S. Pat. No. 4,412,934 to Chung et al., all of which are incorporated herein by reference.

The mole ratio of peroxygen source (as AvO) to bleach activator in the present invention generally ranges from at least 1:1, preferably from about 20:1, more preferably from about 10:1 to about 1:1, preferably to about 3:1.

Quaternary substituted bleach activators can also be included. The present laundry compositions preferably comprise a quaternary substituted bleach activator (QSBA) or a quaternary substituted peracid (QSP, preferably a quaternary substituted percarboxylic acid or a quaternary substituted peroxyimidic acid); more preferably, the former. Preferred QSBA structures are further described in U.S. Pat. No. 5,686,015 to Willey et al.; U.S. Pat. No. 5,654,421 to Taylor et al.; U.S. Pat. No. 5,460,747 to Gosselink et al.; U.S. Pat. No. 5,584,888 to Miracle et al.; U.S. Pat. No. 5,578,136 to Taylor et al.; all of which are incorporated herein by reference.

Highly preferred bleach activators useful herein are amide-substituted as described in U.S. Pat. Nos. 5,698,504; 5,695,679; and 5,686,014, each of which are cited herein above. Preferred examples of such bleach activators include: (6-octanamidocaproyl)oxybenzenesulfonate, (6-nonanamidocaproyl)oxybenzenesulfonate, (6-decanamidocaproyl) oxybenzenesulfonate and mixtures thereof.

Other useful activators are disclosed in U.S. Pat. Nos. 5,698,504; 5,695,679; and 5,686,014, each of which is cited herein above, and in U.S. Pat. No. 4,966,723 to Hodge et al. These activators include benzoxazin-type activators, such as a $C_6H_4$ ring to which is fused in the 1,2-positions a moiety —C(O)OC($R^1$)═N—.

Nitriles, such as acetonitriles and/or ammonium nitriles and other quaternary nitrogen containing nitriles, are another class of activators that are useful herein. Non-limiting examples of such nitrile bleach activators are described in U.S. Pat. Nos. 6,133,216; 3,986,972; 6,063,750; 6,017,464; 5,958,289; 5,877,315; 5,741,437; 5,739,327; 5,004,558; and in EP Nos. 790 244, 775 127, 1 017 773, 1 017 776; and in WO 99/14302, WO 99/14296, WO96/40661, all of which are incorporated herein by reference.

Depending on the activator and precise application, good bleaching results can be obtained from bleaching systems having an in-use pH of from about 6 to about 13, and preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators, as described in U.S. Pat. Nos. 5,698,504; 5,695,679 and 5,686,014, each of which is cited herein above, are very useful herein, especially the acyl caprolactams (see for example WO 94-28102 A) and acyl valerolactams (see U.S. Pat. No. 5,503,639 to Willey et al. incorporated herein by reference).

(b) Organic Peroxides, Especially Diacyl Peroxides—

These are extensively illustrated in Kirk Othmer, Encyclopedia of Chemical Technology, Vol. 17, John Wiley and Sons, 1982 at pages 27-90 and especially at pages 63-72, all incorporated herein by reference. If a diacyl peroxide is used, it will preferably be one which exerts minimal adverse impact on fabric care, including color care.

(c) Metal-Containing Bleach Catalysts—

The compositions and methods of the present invention can also optionally include metal-containing bleach catalysts, preferably manganese and cobalt-containing bleach catalysts.

One type of metal-containing bleach catalyst is a catalyst system comprising a transition metal cation of defined bleach catalytic activity (such as copper, iron, titanium, ruthenium tungsten, molybdenum, or manganese cations), an auxiliary metal cation having little or no bleach catalytic activity (such as zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 to Bragg.

Manganese Metal Complexes—

If desired, the compositions herein can be catalyzed by means of a manganese compound. Such compounds and levels of use are well known in the art and include, for example, the manganese-based catalysts disclosed in U.S. Pat. Nos. 5,576,282; 5,246,621; 5,244,594; 5,194,416; and 5,114,606; and European Pat. App. Pub. Nos. 549,271 A1; 549,272 A1; 544,440 A2; and 544,490 A1. Preferred examples of these catalysts include $Mn(IV)_2(u-O)_3$(1,4,7-trimethyl-1,4,7-triazacyclononane)$_2(PF_6)_2$, $Mn(III)_2(u-O)_1$ $(u-OAc)_2$(1,4,7-trimethyl-1,4,7-triazacyclononane)$_2$ $(ClO_4)_2$, $Mn(IV)_4(u-O)_6$(1,4,7-triazacyclononane)$_4(ClO_4)_4$, $Mn(III)Mn(IV)_4(u-O)_1(u-OAc)_2$-(1,4,7-trimethyl-1,4,7-triazacyclononane)$_2(ClO_4)_3$, Mn(IV)(1,4,7-trimethyl-1,4,7-triazacyclononane)-$(OCH_3)_3(PF_6)$, and mixtures thereof. Other metal-based bleach catalysts include those disclosed in U.S. Pat. Nos. 4,430,243 and 5,114,611. The use of manganese with various complex ligands to enhance bleaching is also reported in the following: U.S. Pat. Nos. 4,728,455; 5,284,944; 5,246,612; 5,256,779; 5,280,117; 5,274,147; 5,153,161; and 5,227,084.

Cobalt Metal Complexes—

Cobalt bleach catalysts useful herein are known, and are described, for example, in U.S. Pat. Nos. 5,597,936; 5,595,967; and 5,703,030; and M. L. Tobe, "Base Hydrolysis of Transition-Metal Complexes", *Adv. Inorg. Bioinorg. Mech.*, (1983), 2, pages 1-94. The most preferred cobalt catalyst useful herein are cobalt pentaamine acetate salts having the formula $[Co(NH_3)_5OAc]$ Ty, wherein "OAc" represents an acetate moiety and "Ty" is an anion, and especially cobalt pentaamine acetate chloride, $[Co(NH_3)_5OAc]Cl_2$; as well as $[Co(NH_3)_5OAc](OAc)_2$; $[Co(NH_3)_5OAc](PF_6)_2$; $[Co(NH_3)_5OAc](SO_4)$; $[Co(NH_3)_5OAc](BF_4)_2$; and $[Co(NH_3)_5OAc](NO_3)_2$ (herein "PAC").

These cobalt catalysts are readily prepared by known procedures, such as taught for example in U.S. Pat. Nos. 6,302,921; 6,287,580; 6,140,294; 5,597,936; 5,595,967; and 5,703,030; in the Tobe article and the references cited therein; and in U.S. Pat. No. 4,810,410; *J. Chem. Ed.* (1989), 66 (12), 1043-45; The Synthesis and Characterization of Inorganic Compounds, W. L. Jolly (Prentice-Hall; 1970), pp. 461-3; *Inorg. Chem.*, 18, 1497-1502 (1979); *Inorg. Chem.*, 21, 2881-2885 (1982); *Inorg. Chem.*, 18, 2023-2025 (1979); *Inorg. Synthesis*, 173-176 (1960); and *Journal of Physical Chemistry*, 56, 22-25 (1952).

Transition Metal Complexes of Macropolycyclic Rigid Ligands—

Compositions herein can also suitably include as bleach catalyst a transition metal complex of a macropolycyclic rigid ligand. The amount used is a catalytically effective amount, suitably about 1 ppb or more, for example up to about 99.9%, more typically about 0.001 ppm or more, preferably from about 0.05 ppm to about 500 ppm (wherein "ppb" denotes parts per billion by weight and "ppm" denotes parts per million by weight).

Transition-metal bleach catalysts of Macrocyclic Rigid Ligands which are suitable for use in the invention compositions can in general include known compounds where they conform with the definition herein, as well as, more preferably, any of a large number of novel compounds expressly designed for the present laundry or laundry uses, and are non-limitingly illustrated by any of the following:

Dichloro-5,12-dimethyl-1,5,8,12-tetraazabicyclo[6.6.2]hexadecane Manganese(II)
Dichloro-5,12-diethyl-1,5,8,12-tetraazabicyclo[6.6.2]hexadecane Manganese(II)
Diaquo-5,12-dimethyl-1,5,8,12-tetraazabicyclo[6.6.2]hexadecaneManganese(II) Hexafluorophosphate
Diaquo-5,12-diethyl-1,5,8,12-tetraazabicyclo[6.6.2]hexadecaneManganese(II) Hexafluorophosphate
Aquo-hydroxy-5,12-dimethyl-1,5,8,12-tetraazabicyclo[6.6.2]hexadecane Manganese(III) Hexafluorophosphate
Diaquo-5,12-dimethyl-1,5,8,12-tetraazabicyclo[6.6.2]hexadecaneManganese(II) Tetrafluoroborate
Dichloro-5,12-dimethyl-1,5,8,12 tetraazabicyclo[6.6.2]hexadecane Manganese(III) Hexafluorophosphate
Dichloro-5,12-diethyl-1,5,8,12-tetraazabicyclo[6.6.2]hexadecane Manganese(III) Hexafluorophosphate
Dichloro-5,12-di-n-butyl-1,5,8,12-tetraaza bicyclo[6.6.2]hexadecane Manganese(II)
Dichloro-5,12-dibenzyl-1,5,8,12-tetraazabicyclo[6.6.2]hexadecane Manganese(II)
Dichloro-5-n-butyl-12-methyl-1,5,8,12-tetraaza-bicyclo[6.6.2]hexadecane Manganese(II)
Dichloro-5-n-octyl-12-methyl-1,5,8,12-tetraaza-bicyclo[6.6.2]hexadecane Manganese(II)
Dichloro-5-n-butyl-12-methyl-1,5,8,12-tetraaza-bicyclo[6.6.2]hexadecane Manganese(II).

As a practical matter, and not by way of limitation, the compositions and methods herein can be adjusted to provide on the order of at least one part per hundred million of the active bleach catalyst species in the composition comprising a lipophilic fluid and a bleach system, and will preferably provide from about 0.01 ppm to about 25 ppm, more preferably from about 0.05 ppm to about 10 ppm, and most preferably from about 0.1 ppm to about 5 ppm, of the bleach catalyst species in the composition comprising a lipophilic fluid and a bleach system.

(d) Bleach Boosting Compounds—

The compositions herein can comprise one or more bleach boosting compounds. Bleach boosting compounds provide increased bleaching effectiveness in lower temperature applications. The bleach boosters act in conjunction with conventional peroxygen bleaching sources to provide increased bleaching effectiveness. This is normally accomplished through in situ formation of an active oxygen transfer agent such as a dioxirane, an oxaziridine, or an oxaziridinium. Alternatively, preformed dioxiranes, oxaziridines and oxaziridiniums can be used.

Among suitable bleach boosting compounds for use in accordance with the present invention are cationic imines, zwitterionic imines, anionic imines and/or polyionic imines having a net charge of from about +3 to about −3, and mixtures thereof. These imine bleach boosting compounds of the present invention include those of the general structure:

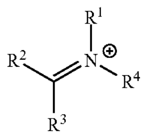

where $R^1$-$R^4$ can be a hydrogen or an unsubstituted or substituted radical selected from the group consisting of phenyl, aryl, heterocyclic ring, alkyl and cycloalkyl radicals.

Among preferred bleach boosting compounds are zwitterionic bleach boosters, which are described in U.S. Pat. Nos. 5,576,282 and 5,718,614. Other bleach boosting compounds include cationic bleach boosters described in U.S. Pat. Nos. 5,360,569; 5,442,066; 5,478,357; 5,370,826; 5,482,515; 5,550,256; and WO 95/13351, WO 95/13352, and WO 95/13353.

Peroxygen sources are well-known in the art and the peroxygen source employed in the present invention can comprise any of these well known sources, including peroxygen compounds as well as compounds, which under consumer use conditions, provide an effective amount of peroxygen in situ. The peroxygen source can include a hydrogen peroxide source, the in situ formation of a peracid anion through the reaction of a hydrogen peroxide source and a bleach activator, preformed peracid compounds or mixtures of suitable peroxygen sources. Of course, one of ordinary skill in the art will recognize that other sources of peroxygen can be employed without departing from the scope of the invention. The bleach boosting compounds, when present, are preferably employed in conjunction with a peroxygen source in the bleaching systems of the present invention.

(e) Preformed Peracids—

Also suitable as bleaching agents are preformed peracids. The preformed peracid compound as used herein is any convenient compound which is stable and which under consumer use conditions provides an effective amount of peracid or peracid anion. The preformed peracid compound can be selected from the group consisting of percarboxylic acids and salts, percarbonic acids and salts, perimidic acids and salts, peroxymonosulfuric acids and salts, and mixtures thereof. Examples of these compounds are described in U.S. Pat. No. 5,576,282 to Miracle et al.

One class of suitable organic peroxycarboxylic acids have the general formula:

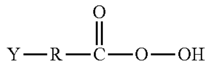

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted peracid has the general formula:

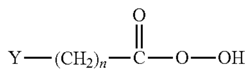

wherein Y can be, for example, H, $CH_3$, $CH_2Cl$, C(O)OH, or C(O)OOH; and n is an integer from 0 to 20. When the organic peroxycarboxylic acid is aromatic, the unsubstituted peracid has the general formula:

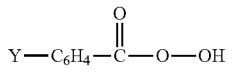

wherein Y can be, for example, hydrogen, alkyl, alkylhalogen, halogen, C(O)OH or C(O)OOH.

Typical monoperoxy acids useful herein include alkyl and aryl peroxyacids such as:

(i) peroxybenzoic acid and ring-substituted peroxybenzoic acid, e.g. peroxy-a-naphthoic acid, monoperoxyphthalic acid (magnesium salt hexahydrate), and o-carboxybenzamidoperoxyhexanoic acid (sodium salt);

(ii) aliphatic, substituted aliphatic and arylalkyl monoperoxy acids, e.g. peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP);

(iii) amidoperoxyacids, e.g. monononylamide of either peroxysuccinic acid (NAPSA) or of peroxyadipic acid (NAPAA).

Typical diperoxyacids useful herein include alkyl diperoxyacids and aryldiperoxyacids, such as:

(i) 1,12-diperoxydodecanedioic acid;

(ii) 1,9-diperoxyazelaic acid;

(iii) diperoxybrassylic acid; diperoxysebacic acid and diperoxyisophthalic acid;

(iv) 2-decyldiperoxybutane-1,4-dioic acid;

(v) 4,4'-sulfonylbisperoxybenzoic acid.

Such bleaching agents are disclosed in U.S. Pat. No. 4,483,781 to Hartman and U.S. Pat. No. 4,634,551 to Burns et al.; European Patent Application 0,133,354 to Banks et al.; and U.S. Pat. No. 4,412,934 to Chung et al. Sources also include 6-nonylamino-6-oxoperoxycaproic acid as described in U.S. Pat. No. 4,634,551 to Burns et al. Persulfate compounds such as for example OXONE, manufactured commercially by E.I. DuPont de Nemours of Wilmington, Del. can also be employed as a suitable source of peroxymonosulfuric acid. PAP is disclosed in, for example, U.S. Pat. Nos. 5,487,818; 5,310,934; 5,246,620; 5,279,757 and 5,132,431.

(f) Photobleaches—

Suitable photobleaches for use in the treating compositions of the present invention include, but are not limited to, the photobleaches described in U.S. Pat. Nos. 4,217,105 and 5,916,481.

(g) Enzyme Bleaching—

Enzymatic systems can be used as bleaching agents. The hydrogen peroxide can also be present by adding an enzymatic system (i.e. an enzyme and a substrate therefore) which is capable of generating hydrogen peroxide at the beginning or during the washing and/or rinsing process. Such enzymatic systems are disclosed in EP Patent Application 91202655.6 filed Oct. 9, 1991.

The present invention compositions and methods can utilize alternative bleach systems such as ozone, chlorine dioxide and the like. Bleaching with ozone can be accomplished by introducing ozone-containing gas having ozone content from about 20 to about 300 g/$m^3$ into the solution that is to contact the fabrics. The gas:liquid ratio in the solution should be maintained from about 1:2.5 to about 1:6. U.S. Pat. No. 5,346,588 describes a process for the utilization of ozone as an alternative to conventional bleach systems and is herein incorporated by reference.

The detergent compositions of the present invention can also include any number of additional optional ingredients. These include conventional laundry detergent composition components such as non-tinting dyes, detersive builders, enzymes, enzyme stabilizers (such as propylene glycol, boric acid and/or borax), suds suppressors, soil suspending agents, soil release agents, other fabric care benefit agents, pH adjusting agents, chelating agents, smectite clays, solvents, hydrotropes and phase stabilizers, structuring agents, dye transfer inhibiting agents, opacifying agents, optical brighteners, perfumes and coloring agents. The various optional detergent composition ingredients, if present in the compositions herein, should be utilized at concentrations conventionally employed to bring about their desired contribution to the composition or the laundering operation. Frequently, the total amount of such optional detergent composition ingredients can range from about 0.01% to about 50%, more preferably from about 0.1% to about 30%, by weight of the composition.

The liquid detergent compositions are in the form of an aqueous solution or uniform dispersion or suspension of surfactant, optical brightener, and certain optional other ingredients, some of which may normally be in solid form, that have been combined with the normally liquid components of the composition, such as the liquid alcohol ethoxylate nonionic, the aqueous liquid carrier, and any other normally liquid optional ingredients. Such a solution, dispersion or suspension will be acceptably phase stable and will typically have a viscosity which ranges from about 100 to 600 cps, more preferably from about 150 to 400 cps. For purposes of this invention, viscosity is measured with a Brookfield LVDV-II+ viscometer apparatus using a #21 spindle.

The liquid detergent compositions herein can be prepared by combining the components thereof in any convenient order and by mixing, e.g., agitating, the resulting component combination to form a phase stable liquid detergent composition. In a preferred process for preparing such compositions, a liquid matrix is formed containing at least a major proportion, and preferably substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactants and the solid form ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills, are incorporated. As a variation of the composition preparation procedure hereinbefore described, one or more of the solid components can be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

In an alternate embodiment for forming the liquid detergent compositions, the optical brightener is first combined with one or more liquid components to form a optical brightener premix, and this optical brightener premix is added to a composition formulation containing a substantial portion, for example more than 50% by weight, more specifically, more than 70% by weight, and yet more specifically, more than 90% by weight, of the balance of components of the laundry detergent composition. For example, in the methodology described above, both the optical brightener premix and the enzyme component are added at a final stage of component additions. In a further embodiment, the optical brightener is encapsulated prior to addition to the detergent composition, the encapsulated optical brightener is suspended in a structured liquid, and the suspension is added to a composition formulation containing a substantial portion of the balance of components of the laundry detergent composition.

As noted previously, the detergent compositions can be in a solid form. Suitable solid forms include tablets and particulate forms, for example, granular particles or flakes. Various techniques for forming detergent compositions in such solid forms are well known in the art and can be used herein. In one embodiment, for example when the composition is in the form of a granular particle, the optical brightener is provided in particulate form, optionally including additional but not all components of the laundry detergent composition. The optical brightener particulate is combined with one or more additional particulates containing a balance of components of the laundry detergent composition. Further, the optical brightener, optionally including additional but not all components of the laundry detergent composition, can be provided in an encapsulated form, and the optical brightener encapsulate is combined with particulates containing a substantial balance of components of the laundry detergent composition.

The compositions of this invention, prepared as hereinbefore described, can be used to form aqueous washing solutions for use in the laundering of fabrics. Generally, an effective amount of such compositions is added to water, preferably in a conventional fabric laundering automatic washing machine, to form such aqueous laundering solutions. The aqueous washing solution so formed is then contacted, preferably under agitation, with the fabrics to be laundered therewith. An effective amount of the liquid detergent compositions herein added to water to form aqueous laundering solutions can comprise amounts sufficient to form from about 500 to 7,000 ppm of composition in aqueous washing solution. More preferably, from about 1,000 to 3,000 ppm of the detergent compositions herein will be provided in aqueous washing solution.

Fabric Care Compositions/Rinse Added Fabric Softening Compositions

In another specific embodiment, the optical brighteners of the present invention can be included in a fabric care composition. The fabric care composition can be comprised of at least one optical brightener and a rinse added fabric softening composition ("RAFS;" also known as rinse added fabric conditioning compositions). Examples of typical rinse added softening compositions can be found in U.S. Provisional Patent Application Ser. No. 60/687,582 filed on Oct. 8, 2004. The rinse added fabric softening composition can comprise from about 1% to about 90% by weight of the FSA, more preferably from about 5% to about 50% by weight of the FSA. The optical brightener can be present in the rinse added fabric softening composition in an amount from about 0.5 ppb to about 50 ppm, more preferably from about 0.5 ppm to about 30 ppm.

In one embodiment of the invention, the fabric softening active (hereinafter "FSA") is a quaternary ammonium compound suitable for softening fabric in a rinse step. In one embodiment, the FSA is formed from a reaction product of a fatty acid and an aminoalcohol obtaining mixtures of mono-, di-, and, in one embodiment, triester compounds. In another embodiment, the FSA comprises one or more softener quaternary ammonium compounds such as, but not limited to, a monoalkyquaternary ammonium compound, a diamido quaternary compound and a diester quaternary ammonium compound, or a combination thereof.

In one aspect of the invention, the FSA comprises a diester quaternary ammonium (hereinafter "DQA") compound composition. In certain embodiments of the present invention, the DQA compounds compositions also encompasses a description of diamido FSAs and FSAs with mixed amido and ester linkages as well as the aforementioned diester linkages, all herein referred to as DQA.

A first type of DQA ("DQA (1)") suitable as a FSA in the present CFSC includes a compound comprising the formula:

$$\{R_{4-m}—N^{+}—[(CH_2)_n—Y—R^1]_m\}X^-$$

wherein each R substituent is either hydrogen, a short chain $C_1$-$C_6$, preferably $C_1$-$C_3$ alkyl or hydroxyalkyl group, e.g., methyl (most preferred), ethyl, propyl, hydroxyethyl, and the like, poly($C_2$-$C_3$ alkoxy), preferably polyethoxy, group, benzyl, or mixtures thereof; each m is 2 or 3; each n is from 1 to about 4, preferably 2; each Y is —O—(O)C—, —C(O)—O—, —NR—C(O)—, or —C(O)—NR— and it is acceptable for each Y to be the same or different; the sum of carbons in each $R^1$, plus one when Y is —O—(O)C— or —NR—C(O)—, is $C_{12}$-$C_{22}$, preferably $C_{14}$-$C_{20}$, with each $R^1$ being a hydrocarbyl, or substituted hydrocarbyl group; it is acceptable for $R^1$ to be unsaturated or saturated and branched or linear and preferably it is linear; it is acceptable for each $R^1$ to be the same or different and preferably these are the same; and $X^-$ can be any softener-compatible anion, preferably, chloride, bromide, methylsulfate, ethylsulfate, sulfate, phosphate, and nitrate, more preferably chloride or methyl sulfate. Preferred DQA compounds are typically made by reacting alkanolamines such as MDEA (methyldiethanolamine) and TEA (triethanolamine) with fatty acids. Some materials that typically result from such reactions include N,N-di(acyl-oxyethyl)-N,N-dimethylammonium chloride or N,N-di(acyl-oxyethyl)-N,N-methylhydroxyethylammonium methylsulfate wherein the acyl group is derived from animal fats, unsaturated, and polyunsaturated, fatty acids, e.g., tallow, hardended tallow, oleic acid, and/or partially hydrogenated fatty acids, derived from vegetable oils and/or partially hydrogenated vegetable oils, such as, canola oil, safflower oil, peanut oil, sunflower oil, corn oil, soybean oil, tall oil, rice bran oil, palm oil, etc.

Non-limiting examples of suitable fatty acids are listed in U.S. Pat. No. 5,759,990 at column 4, lines 45-66. In one embodiment, the FSA comprises other actives in addition to DQA (1) or DQA. In yet another embodiment, the FSA comprises only DQA (1) or DQA and is free or essentially free of any other quaternary ammonium compounds or other actives. In yet another embodiment, the FSA comprises the precursor amine that is used to produce the DQA.

In another aspect of the invention, the FSA comprises a compound, identified as DTTMAC comprising the formula:

$$[R_{4-m}—N^{(+)}—R^1_m]A^-$$

wherein each m is 2 or 3, each $R^1$ is a $C_6$-$C_{22}$, preferably $C_{14}$-$C_{20}$, but no more than one being less than about $C_{12}$ and then the other is at least about 16, hydrocarbyl, or substituted hydrocarbyl substituent, preferably $C_{10}$-$C_{20}$ alkyl or alkenyl (unsaturated alkyl, including polyunsaturated alkyl, also referred to sometimes as "alkylene"), most preferably $C_{12}$-$C_{18}$ alkyl or alkenyl, and branch or unbranched. In one embodiment, the Iodine Value (IV) of the FSA is from about 1 to 70; each R is H or a short chain $C_1$-$C_6$, preferably $C_1$-$C_3$ alkyl or hydroxyalkyl group, e.g., methyl (most preferred), ethyl, propyl, hydroxyethyl, and the like, benzyl, or $(R^2O)_{2-4}H$ where each $R^2$ is a $C_1$-$C_6$ alkylene group; and $A^-$ is a softener compatible anion, preferably, chloride, bromide, methylsulfate, ethylsulfate, sulfate, phosphate, or nitrate; more preferably chloride or methyl sulfate.

Examples of these FSAs include dialkydimethylammonium salts and dialkylenedimethylammonium salts such as ditallowedimethylammonium and ditallowedimethylammonium methylsulfate. Examples of commercially available dialkylenedimethylammonium salts usable in the present invention are di-hydrogenated tallow dimethyl ammonium chloride and ditallowedimethyl ammonium chloride available from Degussa under the trade names Adogen® 442 and Adogen® 470 respectively. In one embodiment, the FSA comprises other actives in addition to DTTMAC. In yet another embodiment, the FSA comprises only compounds of the DTTMAC and is free or essentially free of any other quaternary ammonium compounds or other actives.

In one embodiment, the FSA comprises an FSA described in U.S. Pat. Pub. No. 2004/0204337 A1, published Oct. 14, 2004 to Corona et al., from paragraphs 30-79. In another embodiment, the FSA is one described in U.S. Pat. Pub. No. 2004/0229769 A1, published Nov. 18, 2005, to Smith et al., on paragraphs 26-31; or U.S. Pat. No. 6,494,920, at column 1, line 51 et seq. detailing an "esterquat" or a quaternized fatty acid triethanolamine ester salt.

In one embodiment, the FSA is chosen from at least one of the following: ditallowoyloxyethyl dimethyl ammonium chloride, dihydrogenated-tallowoyloxyethyl dimethyl ammonium chloride, ditallow dimethyl ammonium chloride, ditallowoyloxyethyl dimethyl ammonium methyl sulfate, dihydrogenated-tallowoyloxyethyl dimethyl ammonium chloride, dihydrogenated-tallowoyloxyethyl dimethyl ammonium chloride, or combinations thereof.

In one embodiment, the FSA can also include amide containing compound compositions. Examples of diamide comprising compounds include, but are not limited to, methyl-bis(tallowamidoethyl)-2-hydroxyethylammonium methyl sulfate (available from Degussa under the trade names Varisoft 110 and Varisoft 222). An example of an amide-ester containing compound is N-[3-(stearoylamino)propyl]-N-[2-(stearoyloxy)ethoxy)ethyl)]-N-methylamine.

Another specific embodiment of the invention provides for a rinse added fabric softening composition further comprising a cationic starch. Cationic starches are disclosed in US 2004/0204337 A1. In one embodiment, the rinse added fabric softening composition comprises from about 0.1% to about 7% of cationic starch by weight of the fabric softening composition. In one embodiment, the cationic starch is HCP401 from National Starch.

Suitable Laundry Care Ingredients

While not essential for the purposes of the present invention, the non-limiting list of laundry care ingredients illustrated hereinafter are suitable for use in the laundry care compositions and can be desirably incorporated in certain embodiments of the invention, for example to assist or enhance performance, for treatment of the substrate to be cleaned, or to modify the aesthetics of the composition as is the case with perfumes, colorants, dyes or the like. It is understood that such ingredients are in addition to the components that were previously listed for any particular embodiment. The total amount of such adjuncts can range from about 0.1% to about 50%, or even from about 1% to about 30%, by weight of the laundry care composition.

The precise nature of these additional components, and levels of incorporation thereof, will depend on the physical form of the composition and the nature of the operation for which it is to be used. Suitable laundry care ingredients include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the laundry care ingredients are not essential to Applicants' laundry care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts can be present as detailed below:

Surfactants—

The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—

The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—

The compositions herein can also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—

The compositions of the present invention can also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—

The compositions of the present invention can also contain dispersants. Suitable water-soluble organic materials are the homo- or co-polymeric acids or their salts, in which the polycarboxylic acid can comprise at least two carboxyl radicals separated from each other by not more than two carbon atoms.

Enzymes—

The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—

Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—

Applicants' compositions can include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein can also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and can provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

The following examples further illustrate the subject matter described above but, of course, should not be construed as in any way limiting the scope thereof.

EXAMPLES

The following examples demonstrate the production of capsules according to the invention. The capsules were produced using a triple nozzle coextrusion apparatus such as that depicted in FIG. 4. Different fluids were used to form the core(s), the intermediate layer, and the shell layer of the capsules. Fluid 1, which contained the components that formed the core(s) of the capsules, was pumped through the first nozzle 410. Fluid 2, which contained the components that formed the intermediate layer, was pumped through the second nozzle 420. Fluid 3, which contained the components that formed the shell layer, was pumped through the third nozzle 430. The compositions of the fluids used to produce the capsules in each example are described in further detail below. The three fluids were simultaneously pumped through their respective nozzles so that one or more droplets of Fluid 1 emanating from nozzle 410 was encased in a droplet of Fluid 2 emanating from nozzle 420, which droplet was further encased by a droplet of Fluid 3 emanating from nozzle 430. Each of the resulting "composite" droplets, which would later form the capsule, was allowed to grow until it separated itself from the nozzles due to its growing weight. The droplets were then collected in a bath of cold oil (e.g., corn oil or vegetable oil), in which the components of Fluid 3 solidified to form the shell layer of the capsule. The resulting capsules were then collected and cleaned.

Example 1

This example demonstrates the production of capsules according to the invention having a core containing a polymeric colorant. Specifically, Fluid 1 was a 50 wt. % solution of Liquitint® Violet DD (available from Milliken & Company in Spartanburg, S.C.) in water. Fluid 2 was a silicone oil (i.e., Dow Corning® 200 Fluid 500 cSt) containing approximately 2 wt. % hydrophobic, fumed silica particles (i.e., CAB-O-SIL® TS-720 fumed silica). Fluid 3 was a 3 wt. % solution of agar in water.

Fluids 1 and 2 were delivered to their respective nozzles at room temperature, and Fluid 3 was heated and delivered to the nozzle at a temperature of greater than approximately 60° C. The fluids were passed through the triple nozzle coextrusion apparatus described above, and the droplets emerging from the apparatus were collected in cold corn oil maintained at a temperature of approximately 0-10° C. The components of Fluid 3 coalesced almost instantly on contact with the cold corn oil to form capsules according to the invention. The capsules contained at least one core of the polymeric colorant surrounded by an intermediate silicone layer encased in a solid hydrogel (agarose) shell layer. Following collection and cleaning, some of the resulting capsules were placed in a liquid laundry detergent (i.e., Tide® laundry detergent from The Procter & Gamble Company). The capsules did not burst or leak upon addition to the liquid laundry detergent and remained stable (i.e., did not burst or leak) for several months.

Example 2

This example demonstrates the production of capsules according to the invention having a core containing a polymeric colorant. Specifically, Fluid 1 was a 50 wt. % solution of Liquitint® Violet DD (available from Milliken & Company in Spartanburg, S.C.) in water. Fluid 2 was a silicone oil (i.e., Dow Corning® 200 Fluid 1,000 cSt) containing approximately 2 wt. % hydrophobic silica particles (i.e., Aerosil® 816R silica from Degussa). Fluid 3 was a 3 wt. % solution of agar in water.

Fluids 1 and 2 were delivered to their respective nozzles at room temperature, and Fluid 3 was heated and delivered to the nozzle at a temperature of greater than approximately 60° C. The fluids were passed through the triple nozzle coextrusion apparatus described above, and the droplets emerging from the apparatus were collected in cold corn oil maintained at a temperature of approximately 0-10° C. The components of Fluid 3 coalesced almost instantly on contact with the cold corn oil to form capsules according to the invention. The capsules contained at least one core of the polymeric colorant surrounded by an intermediate silicone layer encased in a solid hydrogel (agarose) shell layer. Following collection and cleaning, some of the resulting capsules were placed in a liquid laundry detergent (i.e., Tide® laundry detergent from The Procter & Gamble Company). The capsules did not burst or leak upon addition to the liquid laundry detergent and remained stable (i.e., did not burst or leak) for several months.

Example 3

This example demonstrates the production of capsules according to the invention having a core containing a polymeric colorant. Specifically, Fluid 1 was a 50 wt. % solution of Liquitint® Violet DD (available from Milliken & Company in Spartanburg, S.C.) in water. Fluid 2 was a silicone oil (i.e., Dow Corning® 200 Fluid 500 cSt) containing approximately 3 wt. % hydrophobic silica particles (i.e., Aerosil® 816R silica from Degussa). Fluid 3 was a 3 wt. % solution of agar in water.

Fluids 1 and 2 were delivered to their respective nozzles at room temperature, and Fluid 3 was heated and delivered to the nozzle at a temperature of greater than approximately 60° C. The fluids were passed through the triple nozzle coextrusion apparatus described above, and the droplets emerging from the apparatus were collected in cold corn oil maintained at a temperature of approximately 0-10° C. The components of Fluid 3 coalesced almost instantly on contact with the cold corn oil to form capsules according to the invention. The capsules contained at least one core of the polymeric colorant surrounded by an intermediate silicone layer encased in a solid hydrogel (agarose) shell layer.

Example 4

This example demonstrates the production of capsules according to the invention having a core containing a polymeric colorant. Specifically, Fluid 1 was a 50 wt. % solution of Liquitint® Violet DD (available from Milliken & Company in Spartanburg, S.C.) in water. Fluid 2 was a silicone oil (i.e., Dow Corning® 200 Fluid 500 cSt) containing approximately 4 wt. % hydrophobic silica particles (i.e., Aerosil® 816R silica from Degussa). Fluid 3 was a 3 wt. % solution of agar in water.

Fluids 1 and 2 were delivered to their respective nozzles at room temperature, and Fluid 3 was heated and delivered to the nozzle at a temperature of greater than approximately 60° C. The fluids were passed through the triple nozzle coextrusion apparatus described above, and the droplets emerging from the apparatus were collected in cold corn oil maintained at a temperature of approximately 0-10° C. The components of Fluid 3 coalesced almost instantly on contact with the cold corn oil to form capsules according to the invention. The capsules contained at least one core of the polymeric colorant surrounded by an intermediate silicone layer encased in a solid hydrogel (agarose) shell layer.

Example 5

This example demonstrates the production of capsules according to the invention having a core containing a polymeric colorant. Specifically, Fluid 1 was a 50 wt. % solution of Liquitint® Violet DD (available from Milliken & Company in Spartanburg, S.C.) in water. Fluid 2 was a silicone oil (i.e., Dow Corning® 200 Fluid 1,000 cSt) containing approximately 2 wt. % hydrophobic silica particles (i.e., Aerosil® 816R silica from Degussa). Fluid 3 was an aqueous solution containing approximately 2 wt. % agar, approximately 1 wt. % sodium polyacrylate (a superabsorbent polymer), and approximately 10 wt. % sodium chloride.

Fluids 1 and 2 were delivered to their respective nozzles at room temperature, and Fluid 3 was heated and delivered to the nozzle at a temperature of greater than approximately 60° C. The fluids were passed through the triple nozzle coextrusion apparatus described above, and the droplets emerging from the apparatus were collected in cold corn oil maintained at a temperature of approximately 0-10° C. The components of Fluid 3 coalesced almost instantly on contact with the cold corn oil to form capsules according to the invention. The capsules contained at least one core of the polymeric colorant surrounded by an intermediate silicone layer encased in a solid hydrogel (agarose) shell layer. Following collection and cleaning, some of the resulting capsules were placed in a liquid laundry detergent (i.e., Tide® laundry detergent from The Procter & Gamble Company). The capsules did not burst or leak upon addition to the liquid laundry detergent. However, once the liquid laundry detergent containing the capsules was diluted with water at a level similar to that encountered in household laundering conditions, the capsules burst and released the polymeric colorant into the water.

Example 6

This example demonstrates the production of capsules according to the invention having a core containing a polymeric colorant. Specifically, Fluid 1 was a 50 wt. % solution of Liquitint® Violet DD (available from Milliken & Company in Spartanburg, S.C.) in water. Fluid 2 was a silicone oil (i.e., Dow Corning® 200 Fluid 1,000 cSt) containing approximately 2 wt. % hydrophobic silica particles (i.e., Aerosil® 816R silica from Degussa). Fluid 3 was an aqueous solution containing approximately 3 wt. % agar, approximately 2 wt. % sodium polyacrylate (a superabsorbent polymer), and approximately 10 wt. % sodium chloride.

Fluids 1 and 2 were delivered to their respective nozzles at room temperature, and Fluid 3 was heated and delivered to the nozzle at a temperature of greater than approximately 60° C. The fluids were passed through the triple nozzle coextrusion apparatus described above, and the droplets emerging from the apparatus were collected in cold corn oil maintained at a temperature of approximately 0-10° C. The components of Fluid 3 coalesced almost instantly on contact with the cold corn oil to form capsules according to the invention. The capsules contained at least one core of the polymeric colorant surrounded by an intermediate silicone layer encased in a solid hydrogel (agarose) shell layer. Following collection and cleaning, some of the resulting capsules were placed in a liquid laundry detergent (i.e., Tide® laundry detergent from The Procter & Gamble Company). The capsules did not burst or leak upon addition to the liquid laundry detergent. However, once the liquid laundry detergent containing the capsules was diluted with water at a level similar to that encountered in household laundering conditions, the capsules burst and released the polymeric colorant into the water.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A capsule comprising:
(a) at least one lipophobic core; and
(b) a continuous shell layer surrounding the core, the shell layer comprising:
(i) a material selected from the group consisting of hydrogels, dehydrated hydrogels, water-soluble polymers, water-dispersible polymers, and combinations thereof; and
(ii) a disintegration aid disposed in the shell layer, the disintegration aid exhibiting an absorption of 5 grams or more of solution per gram of disintegration aid as measured in an aqueous solution having an electrical conductivity of about 5 μS/cm or less, and the disintegration aid being selected from the group consisting of superabsorbent polymers, xerogels, and mixtures thereof.

2. The capsule of claim 1, wherein the water-soluble polymer and water-dispersable polymer are selected from the group consisting of acrylates, polyhydric alcohol, polysaccharides, polyvinyl acetate, polyvinyl pyrrolidone, carboxymethyl cellulose, hydroxyethyl cellulose, acrylamides, acrylates, polyethylene glycols, and mixtures thereof.

3. The capsule of claim 2, wherein the water-soluble polymer is a polyvinyl alcohol.

4. The capsule of claim 1, wherein the continuous shell layer further comprises a gelling agent.

5. The capsule of claim 4, wherein the gelling agent is selected from the group consisting of polysaccharides, gelatin, sodium alginate, agar, carrageenans, and mixtures thereof.

6. A composition comprising at least one surfactant and at least one capsule of claim 1.

7. A cleaning composition comprising at least one cleaning agent and at least one capsule of claim 1.

8. A laundry care composition comprising:
(a) at least one laundry care ingredient; and
(b) at least one capsule, the capsule comprising:
(i) at least one lipophobic core; and
(ii) a continuous shell layer surrounding the core, the shell layer comprising:
(A) a material selected from the group consisting of hydrogels, dehydrated hydrogels, water-soluble polymers, water-dispersible polymers, and combinations thereof; and
(B) a disintegration aid disposed in the shell layer, the disintegration aid exhibiting an absorption of 5 grams or more of solution per gram of disintegration aid as measured in an aqueous solution having an electrical conductivity of about 5 μS/cm or less, and the disintegration aid being selected from the group consisting of superabsorbent polymers, xerogels, and mixtures thereof.

9. The laundry care composition of claim 8, wherein the laundry care ingredient is selected from the group consisting of surfactants, builders, chelating agents, dye transfer inhibiting agents, dispersants, enzymes, enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids, pigments, and mixtures thereof.

10. The laundry care composition of claim 8, wherein the laundry care composition further comprises a liquid medium, the laundry care ingredient is dissolved or dispersed in the liquid medium, and the capsule is suspended in the liquid medium.

11. The laundry care composition of claim 8, wherein the water-soluble polymer and water-dispersable polymer are selected from the group consisting of acrylates, polyhydric alcohol, polysaccharides, polyvinyl acetate, polyvinyl pyrrolidone, carboxymethyl cellulose, hydroxyethyl cellulose, acrylamides, acrylates, polyethylene glycols, and mixtures thereof.

12. The laundry care composition of claim 11, wherein the water-soluble polymer is a polyvinyl alcohol.

13. The laundry care composition of claim 8, wherein the continuous shell layer further comprises a gelling agent.

14. The laundry care composition of claim 13, wherein the gelling agent is selected from the group consisting of polysaccharides, gelatin, sodium alginate, agar, carrageenans, and mixtures thereof.

15. A capsule comprising:

(a) at least one core, the core comprising a lipophobic material;

(b) a continuous, intermediate layer surrounding each core, the intermediate layer comprising a lipophilic material that is immiscible with or insoluble in aqueous media; and (c) a continuous shell layer surrounding the intermediate layer, the shell layer comprising:

(i) a material selected from the group consisting of hydrogels, dehydrated hydrogels, water-soluble polymers, water-dispersible polymers, and combinations thereof; and (ii) a disintegration aid disposed in the shell layer, the disintegration aid exhibiting an absorption of 5 grams or more of solution per gram of disintegration aid as measured in an aqueous solution having an electrical conductivity of about 5 μS/cm or less, and the disintegration aid being selected from the group consisting of superabsorbent polymers, xerogels, and mixtures thereof.

16. The capsule of claim 15, wherein the intermediate layer comprises a lipophilic material selected from the group consisting of vegetable oils, vegetable fats, animal oils, animal fats, mineral oil, paraffinic oils, parrafinic waxes, silicone oils, and mixtures thereof.

17. The capsule of claim 15, wherein the intermediate layer further comprises a hydrophobic, particulate material dispersed in the lipophilic material.

18. The capsule of claim 15, wherein the water-soluble, polymer and water-dispersable, polymer are selected from the group consisting of acrylates, polyhydric alcohol, polysaccharides, polyvinyl acetate, polyvinyl pyrrolidone, carboxymethyl cellulose, hydroxyethyl cellulose, acrylamides, acrylates, polyethylene glycols, and mixtures thereof.

19. The capsule of claim 18, wherein the water-soluble, polymer is a polyvinyl alcohol.

20. The capsule of claim 15, wherein the continuous shell layer further comprises a gelling agent.

21. The capsule of claim 20, wherein the gelling agent is selected from the group consisting of polysaccharides, gelatin, sodium alginate, agar, carrageenans, and mixtures thereof.

22. A composition comprising at least one surfactant and at least one capsule of claim 15.

23. A cleaning composition comprising at least one cleaning agent and at least one capsule of claim 15.

24. A laundry care composition comprising;

(a) at least one laundry care ingredient; and (b) at least one capsule, the capsule comprising:

(a) at least one core, the core comprising a lipophobic material;

(i) a continuous, intermediate layer surrounding each core, the intermediate layer comprising a lipophilic material that is immiscible with or insoluble in aqueous media; and (ii) a continuous shell layer surrounding the intermediate layer, the shell layer comprising:

(A) a material selected from the group consisting of hydrogels, dehydrated hydrogels, water-soluble polymers, water-dispersible polymers, and combinations thereof; and (B) a disintegration aid disposed in the shell layer, the disintegration aid exhibiting an absorption of 5 grams or more of solution per gram of disintegration aid as measured in an aqueous solution having an electrical conductivity of about 5 μS/cm or less, and the disintegration aid being selected from the group consisting of superabsorbent polymers, xerogels, and mixtures thereof.

25. The laundry care composition of claim 24, wherein the laundry care ingredient is selected from the group consisting of surfactants, builders, chelating agents, dye transfer inhibiting agents, dispersants, enzymes, enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids, pigments, and mixtures thereof.

26. The laundry care composition of claim 24, wherein the laundry care composition further comprises a liquid medium, the laundry care ingredient is dissolved or dispersed in the liquid medium, and the capsule is suspended in the liquid medium.

27. The laundry care composition of claim 24, wherein the intermediate layer comprises a lipophilic material selected from the group consisting of vegetable oils, vegetable fats, animal oils, animal fats, mineral oil, paraffinic oils, parrafinic waxes, silicone oils, and mixtures thereof.

28. The laundry care composition of claim 24, wherein the intermediate layer further comprises a hydrophobic, particulate material dispersed in the lipophilic material.

29. The laundry care composition of claim 24, wherein the water-soluble, polymer and water-dispersable, polymer are selected from the group consisting of acrylates, polyhydric alcohol, polysaccharides, polyvinyl acetate, polyvinyl pyrrolidone, carboxymethyl cellulose, hydroxyethyl cellulose, acrylamides, acrylates, polyethylene glycols, and mixtures thereof.

30. The laundry care composition of claim 29, wherein the water-soluble, polymer is a polyvinyl alcohol.

31. The laundry care composition of claim 24, wherein the continuous shell layer further comprises a gelling agent.

32. The laundry care composition of claim 31, wherein the gelling agent is selected from the group consisting of polysaccharides, gelatin, sodium alginate, agar, carrageenans, and mixtures thereof.

* * * * *